US012109318B1

(12) United States Patent
Shultz

(10) Patent No.: US 12,109,318 B1
(45) Date of Patent: Oct. 8, 2024

(54) TOPICAL DRUG DELIVERY DEVICES AND METHODS OF USE

(71) Applicant: MJS Solutions, LLC, Smyrna, GA (US)

(72) Inventor: Jamie Lynn Shultz, Smyrna, GA (US)

(73) Assignee: MJS Solutions, LLC, Smyrna, GA (US)

( * ) Notice: Subject to any disclaimer, the term of this patent is extended or adjusted under 35 U.S.C. 154(b) by 0 days.

(21) Appl. No.: 18/489,631

(22) Filed: Oct. 18, 2023

Related U.S. Application Data

(63) Continuation-in-part of application No. 17/694,312, filed on Mar. 14, 2022.

(60) Provisional application No. 63/209,450, filed on Jun. 11, 2021.

(51) Int. Cl.
*A61K 9/70* (2006.01)
*A61K 9/00* (2006.01)

(52) U.S. Cl.
CPC .......... *A61K 9/7084* (2013.01); *A61K 9/0014* (2013.01)

(58) Field of Classification Search
None
See application file for complete search history.

(56) References Cited

U.S. PATENT DOCUMENTS

| 5,773,022 | A | 6/1998 | Nyqvist-Mayer | |
|---|---|---|---|---|
| 2003/0040706 | A1 | 2/2003 | Kuracina | |
| 2006/0047242 | A1 | 3/2006 | Laurent | |
| 2014/0350526 | A1 | 11/2014 | Makower | |
| 2016/0158523 | A1 | 6/2016 | Helm | |
| 2017/0252556 | A1 | 9/2017 | Bonutti | |
| 2020/0030250 | A1 * | 1/2020 | Decker | ............... A61K 9/7084 |
| 2020/0345890 | A1 | 11/2020 | Olsson | |
| 2021/0007899 | A1 | 1/2021 | Lewis | |
| 2021/0121431 | A1 | 4/2021 | Scherer | |

FOREIGN PATENT DOCUMENTS

| WO | 9526778 | 10/1995 | |
|---|---|---|---|
| WO | WO-2015153899 A1 * | 10/2015 | ............ A61M 35/00 |

* cited by examiner

*Primary Examiner* — Isis A Ghali
(74) *Attorney, Agent, or Firm* — PABST PATENT GROUP LLP

(57) ABSTRACT

Devices, groups of devices, kits, and methods for using the devices and kits to administer a local anesthetic to a port site to numb the site prior to infusion or blood draw are described. The devices contain a flexible material with an adhesive coating on one side and a compartment for containing the medication. The device can be pre-filled or a fillable device. In fillable devices, the local anesthetic is transferred from a container into the compartment of the device via the inlet after the device is applied to the patient's skin. In pre-filled devices, the local anesthetic is inside the compartment and is covered with a removable layer to keep it sterile until use. When applied to the patient's skin, the device conforms to the surface of the patient's skin forming a seal keeping the medication in contact with port site.

16 Claims, 13 Drawing Sheets

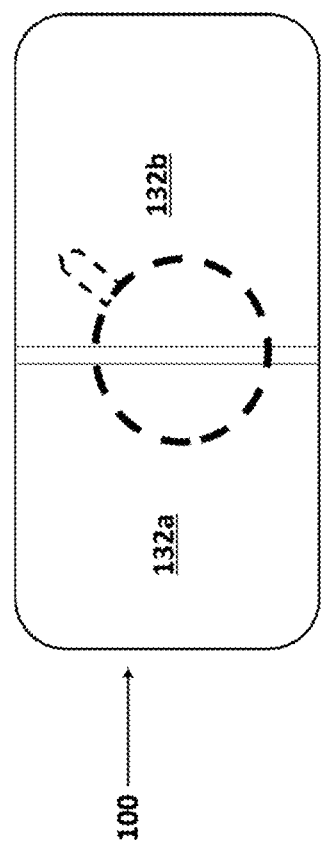
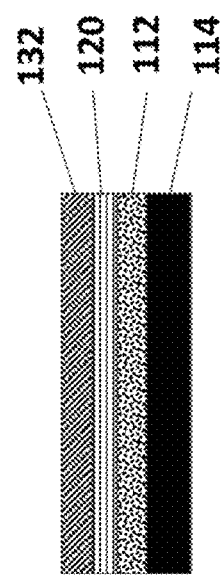

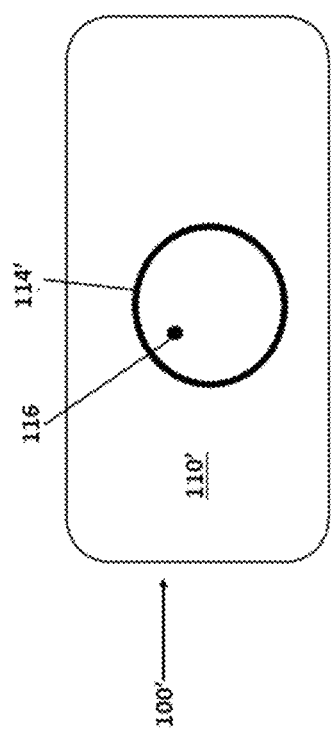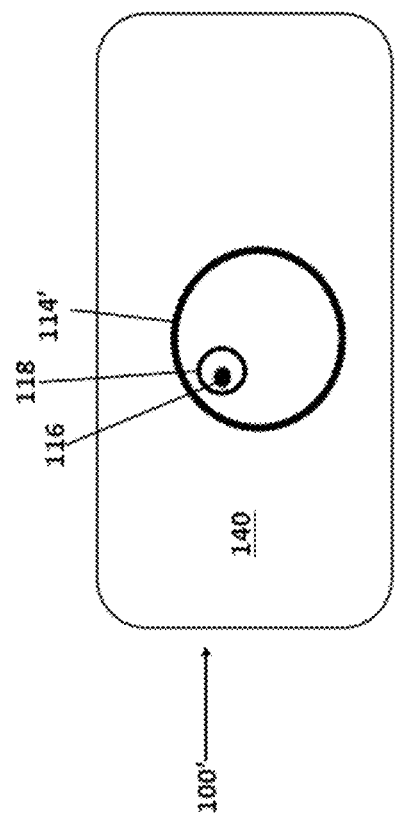

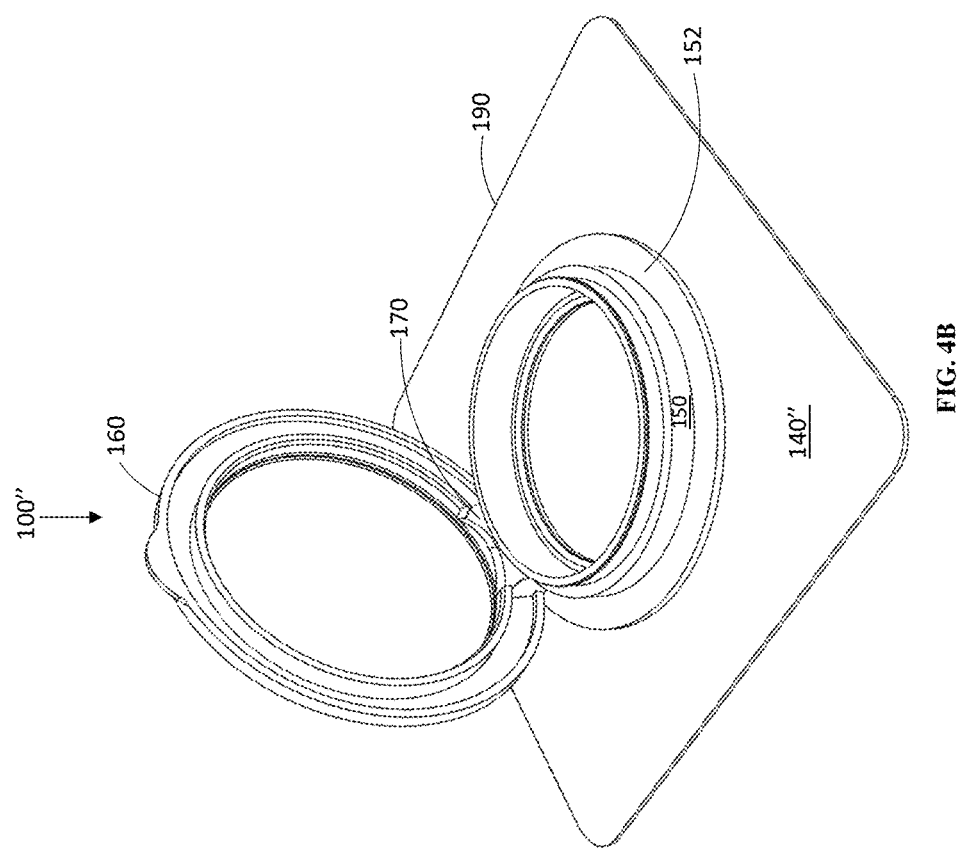
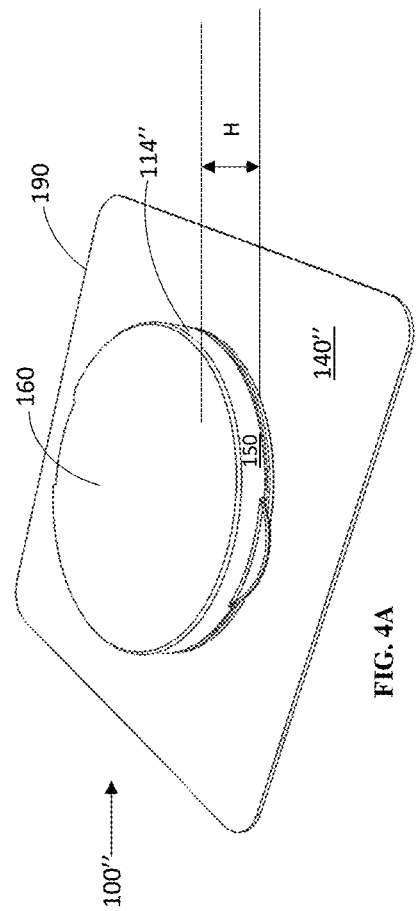

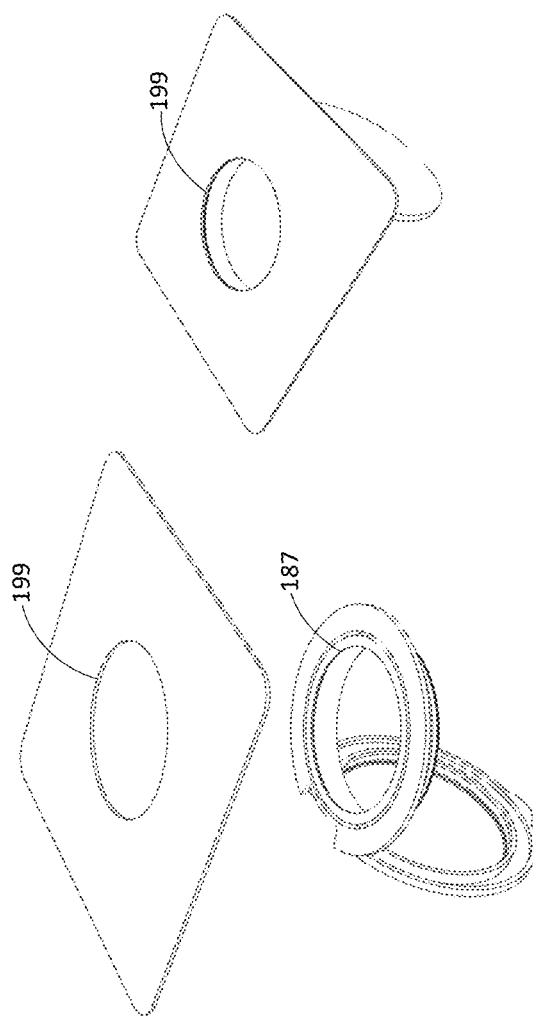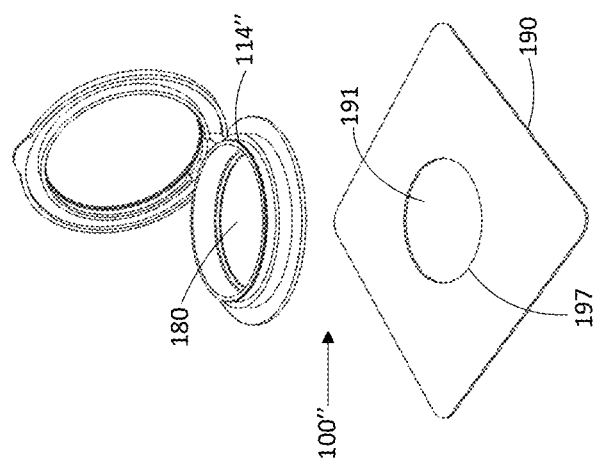

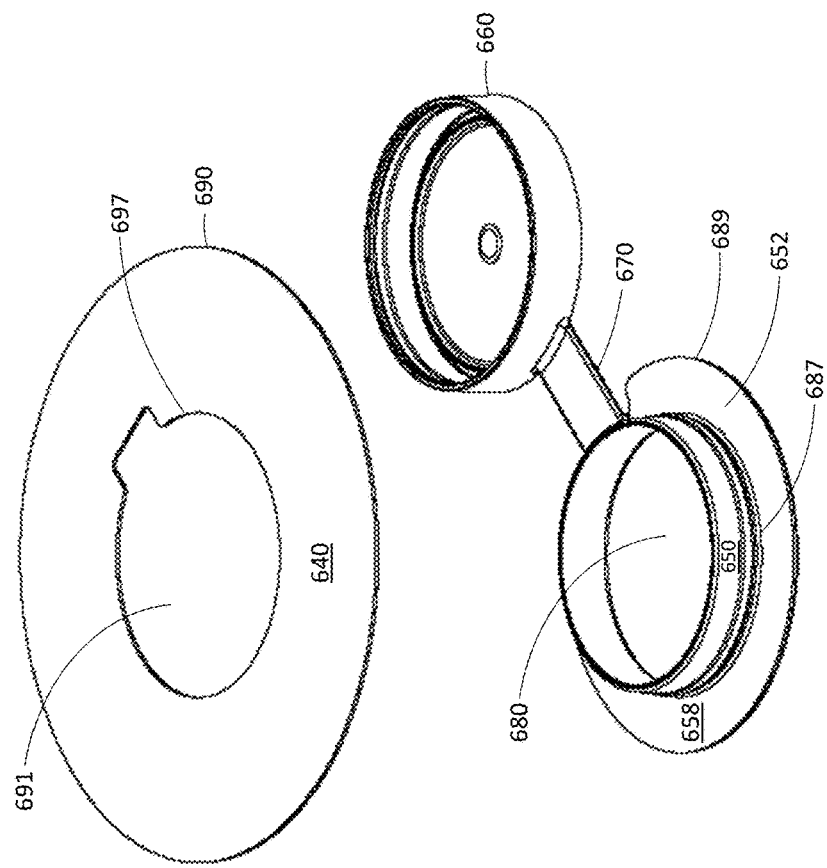
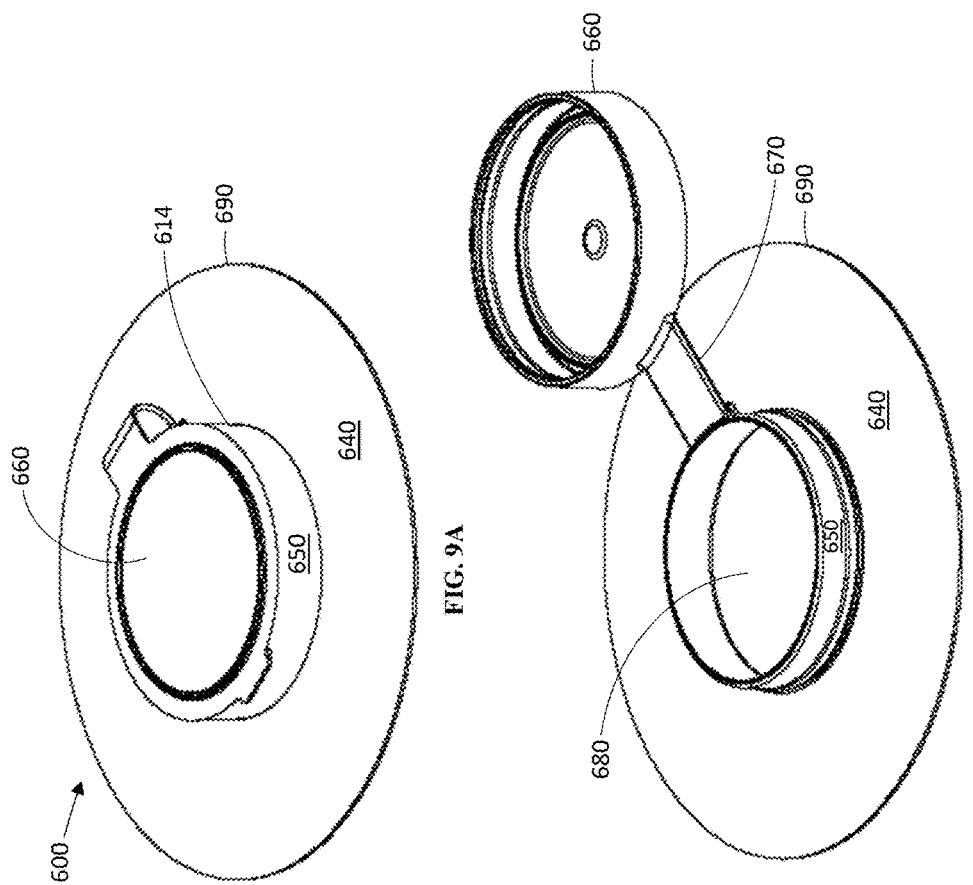
FIG. 9A
FIG. 9B
FIG. 9C

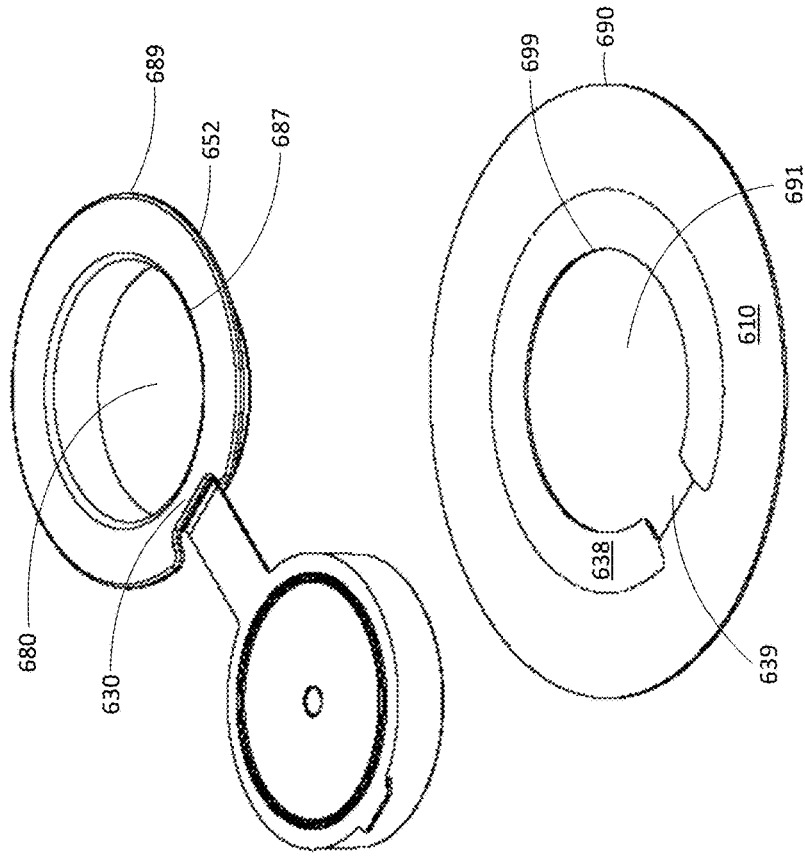
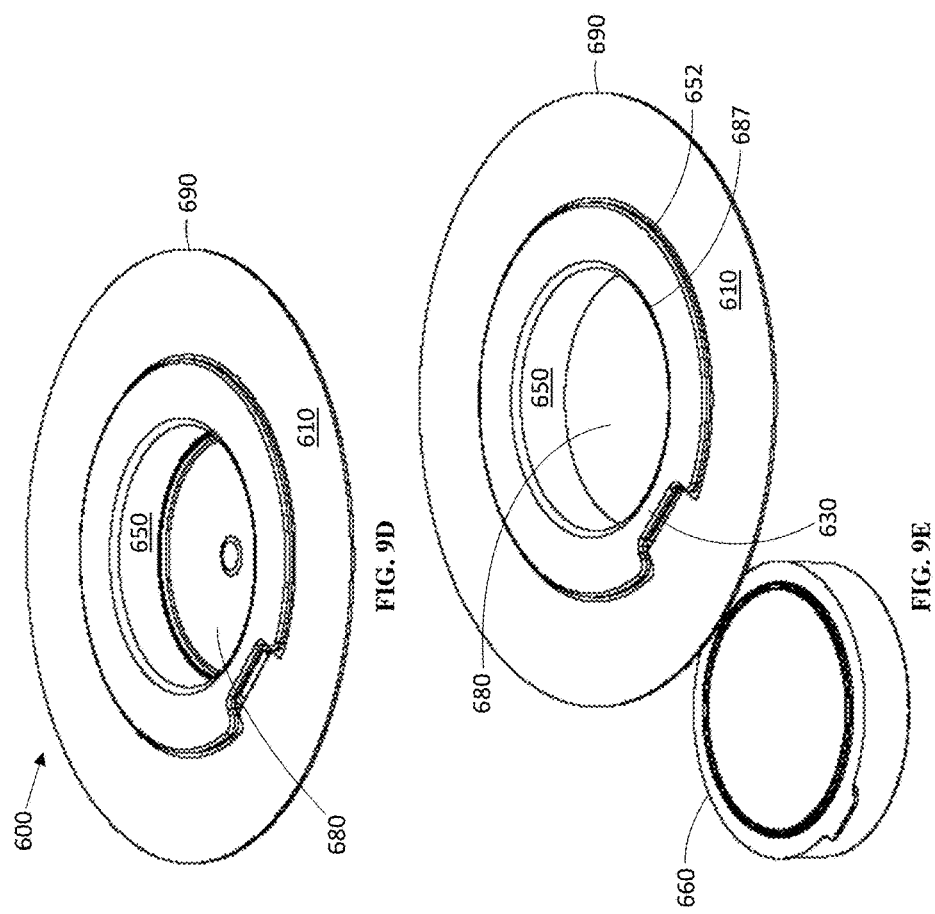
FIG. 9D
FIG. 9E
FIG. 9F

TOPICAL DRUG DELIVERY DEVICES AND METHODS OF USE

CROSS REFERENCE TO RELATED APPLICATION

This application is a continuation-in-part of U.S. application Ser. No. 17/694,312, filed Mar. 14, 2022, which claims priority to and the benefit of U.S. Provisional Application No. 63/209,450, filed Jun. 11, 2021, the disclosures of which are incorporated herein by reference in their entirety.

FIELD OF THE INVENTION

This invention is generally in the field of methods and devices for topical delivery of active agents, particularly anesthetics.

BACKGROUND OF THE INVENTION

Individuals who require frequent intravenous delivery of medicine or blood draws often have an infusion port implanted beneath their skin, such as in the upper chest or underside of the upper arm. Infants, children, and adults use chest ports to manage chronic illness, such as cancer and autoimmune and neurological disorders.

An infusion port allows medical professionals easy, reliable access to administer medicine, vitamins, and/or other necessary liquids to a patient directly into the veins. An infusion port also allows medical professionals the ability to withdraw blood from a patient for labs. It makes taking blood samples easier and is generally more comfortable for the patient than multiple needle sticks. The port also protects a patient's veins as some medications are too corrosive to be injected into a peripheral vein.

A port can remain in place as long as necessary, such as for a short term, for example, a few hours or days, or for a long term, for example, several weeks, months or even years.

An implanted port typically contains a portal with a raised septum, which is connected to a catheter. The portal is the starting point of fluid flow through the catheter. The septum provides an access point and is made from a self-sealing silicone material that can be punctured by a needle repeatedly before the strength of the material is compromised.

The catheter is a small, plastic, flexible tube. One end of the catheter is connected to the port, and the other end is threaded into and sits in a central vein, such as the jugular vein, subclavian vein, or the superior vena cava.

Often prior to departing for an infusion and prior to port access, a local anesthetic is applied to the surface of skin at the port site. For example, patients may self-administer topical lidocaine cream to the port site, cover it with plastic wrap to keep the cream at the site of application to enhance cutaneous absorption. Patients typically allow the cream to remain on the site for at least 10 minutes to one hour prior to receiving an infusion at a hospital or clinic. By applying the local anesthetic prior to arriving at the hospital or clinic, the local anesthetic is delivered to the skin at a sufficient depth at the port site for a sufficient period of time to achieve analgesia in the skin at the port site prior to injection.

However, this process is cumbersome and messy, and is particularly challenging for an individual to practice and/or administer on their own, without assistance. For example, patients need to cut a piece of plastic wrap, such as Saran Wrap or Cling Wrap, and then eventually apply it to cover the port site after application of a topical anesthetic formulation, such as lidocaine cream. However, the plastic wrap is difficult to cut and to stick to the skin. Further, patients often experience issues when self-applying the lidocaine cream as it is runny and often runs off of the port site before the plastic wrap is applied to the port site. When applying the plastic wrap, the patient or others that assist the patient may get the anesthetic on their hands and subsequently, upon touching, to other body parts, such as in eyes, ears, nose, mouth, or on skin that has open cuts or scrapes, which is unsafe. Further, it is difficult for patients with the plastic wrap on to drive to treatment, as the seatbelt usually rubs against the plastic wrap and pulls the wrap off the patients' skin.

In addition to the challenges listed above, the topical anesthetic in a liquid formulation needs to remain in contact with the patient's port site prior to applying the plastic wrap and throughout the time period that the plastic wrap remains over the port site. The topical anesthetic cannot be rubbed in or absorbed via a bandage. However, application of the plastic wrap often causes the topical anesthetic formulation to shift beyond the location of the port site, making the anesthetic ineffective at the port site, i.e. it does not achieve analgesia in the skin at the port site prior to injection.

It is an object of the invention to provide improved methods for topically administering a medication, such as a local anesthetic to a patient.

It is a further object of the invention to provide a device to facilitate the topical application, particularly self-application of a medication, particularly a local anesthetic, to a patient.

It is a further object of the invention to provide a kit to facilitate the topical application, particularly self-application of a medication, particularly a local anesthetic, to a patient.

SUMMARY OF THE INVENTION

Devices, groups of devices, kits, and methods for using the devices and kits to administer a local anesthetic to a port site to numb the site prior to infusion or blood draw are described. The devices contain a flexible material with an adhesive coating on one side and a compartment for containing a topical formulation comprising the local anesthetic. The compartment attaches to the front side of the flexible material. The compartment contains an opening that aligns with a through hole in the flexible material. The adhesive is covered with a removable, protective layer. The device can be pre-filled with the topical formulation or it can be a fillable device. In fillable devices, the topical formulation containing the local anesthetic is transferred from a container into the compartment of the device via the inlet after the device is applied to the patient's skin. In pre-filled devices, the topical formulation containing the local anesthetic is inside the compartment and is covered with a removable layer to keep it sterile until use. When applied to the patient's skin, the border of the through hole in the flexible material conforms to the surface of the patient's skin forming a seal keeping the medication in contact with the port site to numb the site.

BRIEF DESCRIPTION OF THE DRAWINGS

FIGS. 1A-1D are different views of the back side of an exemplary device for topically administering a medication which is pre-filled with the medication. FIG. 1A illustrates the back side of the device immediately prior to application to the skin. FIG. 1B illustrates the back side of the device with a removable layer covering the opening to the compartment containing the medication. FIG. 1C illustrates the back side of the device with a removable protective layer to protect the adhesive layer of the device. The dashed lines indicate the location of the removable layer with a tabbed portion covering the opening to the compartment. FIG. 1D is a cross-sectional view of the layers of materials inside the compartment, including the compartment, as depicted in FIG. 1C. The top, outer layer is the removable, protective layer; the next layer is the removable layer covering the opening to the compartment; the next layer is the medication; and the final layer is the flexible, inert container.

FIGS. 2A-2C are different views of another exemplary device, which can be filled with the medication after the device is applied to the patient's skin. FIG. 2A illustrates the back side of the device immediately prior to application to the skin. The container is empty; it does not contain any medication. FIG. 2B illustrates the front side of the device, showing the connector inlet, which is configured to mate with the outlet of a container containing the medication to be administered to the patient. FIG. 2C illustrates the back side of the device prior to application on the port site of a patient with a removable protective layer to protect the adhesive layer of the device.

FIGS. 4A-4E are different views of another embodiment of an exemplary device that can be filled with the topical formulation after the device is applied to the patient's skin. This exemplary device contains a cap that is hingedly connected to a side wall of the compartment, where the cap is able to open and close via the hinge. FIG. 4A illustrates a top perspective view of the front side of the device, where the cap is in the closed position. FIG. 4B illustrates a top perspective view of the front side of the device depicted in FIG. 4A with the cap in an open position. FIG. 4C illustrates an exploded view of the front side of the device depicted in FIG. 4B. FIG. 4D illustrates an exploded view of the back side of the device depicted in FIG. 4B. FIG. 4E illustrates a perspective view of the back side of the device depicted in FIG. 4B.

FIG. 8A illustrates a top perspective view of the front side of another embodiment of the device, where the cap is in the closed position. FIG. 8B illustrates a top perspective view of the front side of the device of FIG. 8A with the cap in an open position. FIG. 8C is a perspective, exploded view of the back side of the device of FIG. 8A. FIG. 8D is a perspective, exploded view of the front side of the device of FIG. 8A.

FIGS. 9A-9F are different views of another embodiment of an exemplary device that can be filled with the topical formulation after the device is applied to the patient's skin. FIG. 9A illustrates a top perspective view of the front side of the exemplary device, where the cap is in the closed position. FIG. 9B illustrates a top perspective view of the front side of the exemplary device, where the cap is in the open position. FIG. 9C is an exploded view of the front side of the exemplary device. FIG. 9D illustrates a bottom perspective view of the back side of the exemplary device, where the cap is in the closed position. FIG. 9E illustrates a bottom perspective view of the back side of the exemplary device, where the cap is in the open position. FIG. 9F is an exploded view of the back side of the exemplary device.

DETAILED DESCRIPTION OF THE INVENTION

I. Devices

Figure 1A:
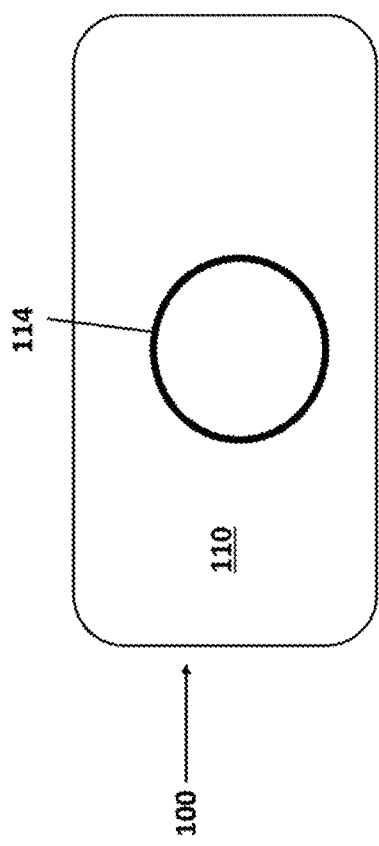

The device contains a flexible material with an adhesive coating on one side and a compartment for containing a topical medication. The flexible material and the compartment can be two or more separate components that connect to each other or a unitary piece. For example, the compartment and flexible material are two separate pieces, where the compartment attaches to the flexible material by glue or mechanical assembling. For example, the compartment and flexible material is a unitary piece that is formed by molding or 3D printing. Regardless of whether the compartment and the flexible material are separate compartments or a unitary piece, they can be made from the same material or different materials. For example, the compartment and flexible material are two separate pieces, where a first piece is made from a material that is the same as or different from the material forming the second piece. For example, the compartment and flexible material is a unitary piece that is formed by molding, where the material forming the compartment is the same or different from the material forming the flexible material.

The flexible material contains a front side and a back side, where the back side contains the adhesive coating. The compartment is attached to or integrated with the front or back side of the flexible material. For example, when the flexible material and compartment are separate components, the compartment is attached to the front or back side of the flexible material by a suitable means, such as by glue or mechanical assembling. When the flexible material and the compartment is a unitary piece, the compartment is integrated with the front side of the flexible material. Generally, the side wall of the compartment is raised relative to the front side of the flexible material.

The adhesive allows the device to adhere to the patient's skin and be removed therefrom within about 1 hour after application. Prior to use, the adhesive is covered with a removable, protective layer, such as wax-coated paper.

The device also contains a compartment configured to contain the local anesthetic. In fillable devices, the compartment is empty, and is filled with the local anesthetic after the device is applied to the patient's skin. In pre-filled devices, the compartment is filled with the local anesthetic prior to application of the device to the patient. It is understood that in place of or in addition to local anesthetics, the device can be filled with another liquid medication or supplements for delivery to a patient over the port site on the patient's skin, such as vitamins and other liquids, based on the need and condition of the patient.

The compartment is typically formed of an inert, biocompatible material. In some embodiments, the compartment is formed from a flexible inert material, such as silicone.

In some embodiments, such as in fillable devices, the compartment is defined by side walls and a top. Opposite the top is an opening.

The opening of the compartment (see, e.g., FIG. 4E, 180) is defined by one or more borders (see, e.g., FIG. 4E, 187) of the compartment. The flexible material contains a through hole (see, e.g., FIG. 4C, through hole 191), which is defined by a front border (see, e.g., FIG. 4C, 197) on the front side of the flexible material and a back border (see, e.g., FIG. 4E, 199) on the back side of the flexible material. The through hole defines the shape of the opening that is exposed to the patient's skin when the device is applied over the port site of the patient.

The compartment is attached to the front side of the flexible material and is positioned such that at least a portion of the opening of the compartment aligns with the through hole, to allow the medication inside the compartment to contact the port site of the patient (though the though hole), when the device is in use. Optionally, the opening of the compartment aligns with the through hole. When applied on the patient's skin over the port site, the back border of the through hole of the flexible material conforms to the surface of the patient's skin, forming a seal to prevent medication inside the compartment from spreading to areas of the patient's skin located outside of the port site.

In some embodiments, the shape and dimensions of the through hole in the flexible material correspond with the shape and dimensions of the opening of the compartment, and optionally the border of the opening aligns with the front border of the through hole. For examples, as shown in FIGS. 4C and 4D, the through hole 191 of flexible material 190 has a shape and size that correspond to the shape and size of opening 180 of the compartment. The compartment 114" is attached to the front side 140" of the flexible material, such as via a suitable adhesive. The border 187 of the compartment aligns with the front border 197 of the through hole. Accordingly, the opening 180 of the compartment aligns with the through hole 191 of the flexible material. Upon removal of a protective layer, the opening 180 of the compartment is exposed on the back side of the device (via the through hole) (see, e.g., FIG. 4E). After the device is applied over the port site of a patient, the back border 199 of the through hole of the flexible material conforms to the surface of the skin and thereby forms a seal. The medication inside the compartment contacts the port site of the patient (through the opening and through hole) when the device is in use.

Generally, the compartment does not contain an absorbent material, such as a pad, for example, a foam pad or sterile pad. The topical formulation is not in an absorbent material. Thus, when applied to the patient's skin, the medication is in direct contact with the port site.

Prior to use, at least the adhesive portion of the back side of the device is covered with a removable, protective layer. Optionally, the entire back side of the device is covered with a protective layer. The protective layer can be formed of one or more separate parts, optionally two separate parts.

In embodiments where the compartment is pre-filled with a local anesthetic, or another liquid medication/supplement, prior to use, the through hole on the back side of the flexible material is covered with an inert, removable layer, such as a foil layer, that seals the local anesthetic inside the compartment and keeps the medication sterile until the removable layer is removed. The removable layer may include a tab portion to facilitate pulling the layer off of the opening to the compartment. Alternatively, the removable layer breaks open upon application of a pressure by a user to release the medication in the compartment. Exemplary suitable materials for forming such a removable layer include, but are not limited to, Fabripore tape (Areza Medical), micropore tape (3M), transpore tape (3M), and other porous acrylics that have a Moisture Vapor Transmission Rate (MVTR) similar to the MVTR of Fabripore tape (Areza Medical), micropore tape (3M), and/or transpore tape (3M). For example, the removable layer is formed of a Fabripore tape (Areza Medical), a micropore tape (3M), or a transpore tape (3M), which breaks open when the user manually applies a pressure on the flexible material and/or compartment, such as by squeezing or pressing the flexible material and/or compartment, and releases the medication from the compartment.

A. Size and Shape

The device can be in any suitable shape, such as a square, rectangle, circle, and other regular shapes or an irregular shape.

The overall dimensions of the device are selected to cover the port site and provide a sufficient surface area of the adhesive portion to adhere the device to the patient's skin, while also allowing for easy removal of the device when desired.

The adhesive portion generally surrounds the compartment. Typically, the surface area of the device is about 20% to about 150% greater, about 50% to about 150% greater, about 20% to about 100% greater, about 20% to about 90% greater, about 50% to about 100% greater, about 40% to about 90% greater, about 50% to about 90% greater, about 70% to about 90% greater, about 70% to about 100% greater, or about 70% to about 150% greater, than the surface area of the opening of the compartment.

For example, if the device is in the shape of a rectangle, typical dimensions for the device include a length ranging from about 2.5 inches to about 5 inches, from about 3 inches to about 5 inches, from about 3 inches to about 4.5 inches, or from about 4 inches to about 5 inches, and a width ranging from about 1.5 inches to about 4 inches, from about 2 inches to about 4.5 inches, from about 2.5 inches to about 4 inches, or from about 2.5 inches to about 3 inches. For example, the device can have dimensions of about 4.5 inches by about 3 inches, optionally the compartment is in the shape of a circle and has a diameter of about 1.5 inches.

For example, if the device is in the shape of a circle, typical dimensions for the device include diameters that are about 20-100% greater than the diameter of the compartment. For example, for compartments having a diameter in the range of about 1 to about 2 inches, the diameter of the device can range from about 1.2 to about 4 inches, such as from about 1.2 to about 2 inches, from about 1.5 to about 2 inches, from about 1.7 to about 2.5 inches, from about 2 to about 3 inches, from about 2 to about 4 inches, from about 2.4 to about 3 inches, from about 2.5 to about 3 inches, from about 2.5 to about 4 inches, or from about 3 to about 4 inches.

B. Compartment

The compartment is typically formed from an inert silicon or plastic, such as polycarbonate, polypropylene, polyethylene (e.g. high density polyethylene). The compartment can be a unitary piece or formed by assembling two or more separate parts together. When the compartment is formed by assembling two or more parts, each part can be made from the same material or one or more of the parts can be made from different materials.

In fillable embodiments, the compartment is typically defined by one or more side wall(s) and a top. Opposite the top is an opening defined by a border. The compartment is configured to contain the medication and fit over the port site. The opening of the compartment has a suitable size and shape for fitting over the port site, such as a square, triangle, diamond shape, rectangle, circle, and other regular and irregular shapes. Typical diameters for the opening of the compartment range from about 1 inch to about 2 inches, from about 1 inch to about 1.5 inches, from about 1 inch to about 1.4 inches, from about 1 inch to about 1.3 inches, from about 1 inch to about 1.2 inches, such as for example about 1.1 inches or about 1.5 inches. The compartment can have any suitable shape, such as a square, triangle, diamond shape, rectangle, circle, and other regular and irregular shapes, as long as it fits over the port site.

The compartment is attached to the front side of the flexible material, where at least a portion of the opening aligns with a though hole of the flexible material. When the device is placed on a patient's skin over the port site, the portion of the opening of the compartment aligned with the through hole is exposed to the patient's skin via the through hole, and thereby allows the medication to contact the port site through the opening and the through hole. In some embodiments, the opening of the compartment has a shape and size corresponding to the shape and size of the through hole. In these embodiments, the border of the compartment aligns with the front border of the through hole, such that when applied to the port site of the patient, the entire opening is exposed to the patient's skin via the through hole. Typically, the compartment has a circular cross-section. Typical diameters for the compartment range from about 1 inch to about 2 inches, such as for example about 1.5 inches. Optionally, the compartment can be smaller, such as from approximately 1 inch to 1.5 inches in diameter, optionally from 1 inch to 1.4 inches, from 1 inch to 1.3 inches, or from 1 inch to 1.2 inches in diameter.

In embodiments in which the compartment is empty and does not contain the medication prior to application on the patient's skin (i.e. a fillable device), the top of the compartment is configured such that it allows the medication to be transferred into the compartment. After the compartment is filled and the top is in the closed position, the opening of the compartment is opposite the top. At least a portion of the opening of the compartment aligns with the through hole of the flexible material and thereby is exposed to the patient's skin, which allows the medication to be in direct contact with the port site (through the opening of the compartment and the through hole of the flexible material).

For example, in some embodiments of the fillable device, the top of the compartment includes an inlet connector on the front side of the device, which allows the medication to be transferred into the compartment. The inlet connector is configured to mate with the outlet of a container containing the medication to be administered to the patient. The inlet connector includes an inlet opening which connects to the inside of the compartment. When the container containing the medication is connected to the inlet connector and the medication is squeezed or pushed out of the container, the medication enters the compartment of the device via the inlet opening. Optionally the inlet opening comprises a one-way valve or is self-sealing. Optionally the inlet opening is raised relative to the outer surface of the compartment. Typically, the inlet connector and inlet opening are formed from silicon.

Alternatively, in other embodiments of the fillable device, the top of the compartment is in the form of a cap that is removable from the rest of the device or is hingedly attached to a portion of the device, such as a side wall of the compartment, and able to open and close via the hinge. In these embodiments, the compartment of the fillable device is defined by one or more side walls and a cap. The cap of the compartment is formed by a plastic, such as polycarbonate, polypropylene, polyethylene (e.g. high density polyethylene).

Optionally, the cap includes a window to provide visual access to the inside of the compartment when the device is in use.

Figure 5:
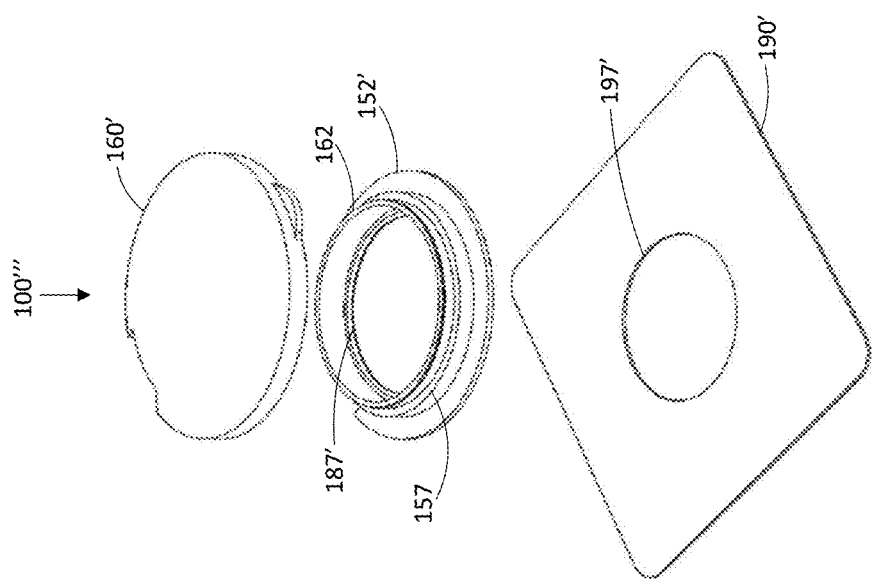
FIG. 5 is an exploded view of another embodiment of an exemplary fillable device, which contains a cap that is removable from the device and attaches to the device, such as by being screwed on using mating threads, where the mating threads are included on a flange portion that is attached to the flexible material.

In some embodiments, the cap is removable from the device and attaches to the device, such as by being screwed on using mating threads, where the mating threads are included on a bottom portion that is attached to the flexible material (see, e.g., FIG. 5). When the cap is screwed on the bottom portion, these two parts form the compartment, which is defined by a side wall and a removable cap. The cap and the bottom portion can be formed by the same material or different materials. For example, the cap is formed by polypropylene (PP) and the bottom portion is formed by polyethylene tetra-ethylene (PETE). Optionally, the bottom portion includes a flange at its base. The flange is configured to provide additional support to the device, thereby facilitating attachment to and removal of the device from the patient's skin.

Although not shown, other mechanisms can be used to attach a removable cap to the device. For example, the cap is removable from the device and attaches to the device by applying a manual force on the cap, such as by flipping open the cap to detach it from the device and pushing down the cap to attach it on a bottom portion attached on the flexible material using a manual force. The cap and the bottom portion can be formed by the same material or different materials.

Optionally, the cap is hingedly connected with a portion of a side wall of the compartment, such that it can open and close via the hinge (see, e.g., FIG. 4A-4B). In such embodiments, the compartment is formed from a unitary piece, since the cap is attached to a side wall. The cap hingedly connected to the side wall of the compartment can be opened and closed using any suitable mechanism. In some forms, a manual force is applied on the hingedly attached cap to open or close the cap. For example, the cap is opened by flipping open the cap, or is closed by pushing down the cap.

Optionally, the compartment includes a flange at its base (see, e.g., FIG. 4B, 152). The flange may attach to the front side of the flexible material or to the back side of the flexible material, such as via attachment to the adhesive on the back side of the flexible material.

Figure 6:
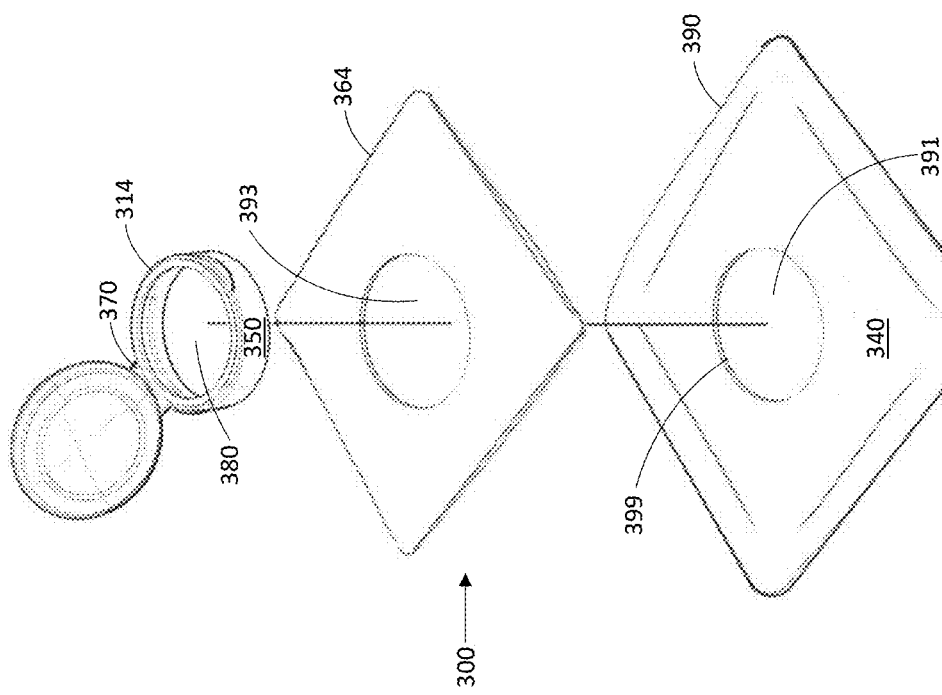
FIG. 6 is an exploded view of another embodiment of an exemplary fillable device, which contains a cap that is hingedly connected to a side wall of the compartment. The cap is able to open and close using the hinge. A foam pad is sandwiched between the compartment and the flexible material.

Optionally, a flexible sealant, such as a foam material (e.g. a foam pad), is located between the compartment and the flexible material (see, e.g., FIG. 6). In these embodiments, a flange included at the base of the compartment may attach to the front side of the flexible material, to the flexible sealant that attaches to the front side of the flexible material, or to the back side of the flexible material, such as by attaching to the adhesive on the back side of the flexible material. The foam material has a suitable size, shape, and thickness to provide structural support to the compartment and optionally prevent leakage of the medication from inside of the compartment. When more than one sealant material is included in the device, each foam material can have a size, shape, and/or thickness that is the same as or different from the other(s). The foam material includes a through hole that has a suitable shape and dimensions sufficient to provide a seal surrounding the opening of the compartment. For example, as shown in FIG. 6, a foam pad 364 contains a second through hole 393, which helps form a seal surrounding the opening 380 of the compartment, when the device is applied to the patient's skin. The second through hole 393 aligns with the opening 380 of the compartment and the through hole 391 of the flexible material.

In another example, the compartment is formed of at least two parts, a top portion and a bottom portion, optionally where the bottom portion contains a flange that is proximal to the flexible material. The side wall can be formed when the top portion containing a top side wall is joined with the bottom portion, which contains a bottom side wall. The bottom side wall typically corresponds with the inner surface of the side wall, while the top side wall typically corresponds with the outer surface of the side wall for the compartment. Alternatively, the compartment can be configured such that the top side wall corresponds with the inner surface of the side wall and the bottom side wall corresponds with the outer surface of the side wall.

Optionally, the top portion contains top side wall(s) and the cap is hingedly connected with a portion of the top side wall(s) of the top portion. The bottom portion contains bottom side wall(s) and the opening, and optionally a flange at its base. In these embodiments, the top portion and bottom portion each contain mating threads, allowing the top portion to be screwed onto the bottom portion. When the top portion is attached to the bottom portion, these two parts form the compartment of the device, where the top side wall (see, e.g., FIG. 7A, 486) of the top portion and the bottom side wall (see, e.g., FIG. 7A, 496) of the bottom portion together form the side wall of the compartment.

The top portion and the bottom portion can be formed by the same material or different materials. For example, the top portion is formed by polypropylene (PP) and the bottom portion is formed by polyethylene tetra-ethylene (PETE).

Typically, the compartment has a height (H) of up to about 2.5 cm, measured from the front side of the flexible material to the top of the compartment (see, e.g., FIG. 4A, H). For example, the height (H) of the compartment is from about 1 cm to about 2.5 cm, from about 1 cm to about 2 cm, from about 1 cm to about 1.5 cm, from about 1.5 cm to about 2.5 cm, or from about 1.5 cm to about 2 cm.

1. Flange

Figure 7A:
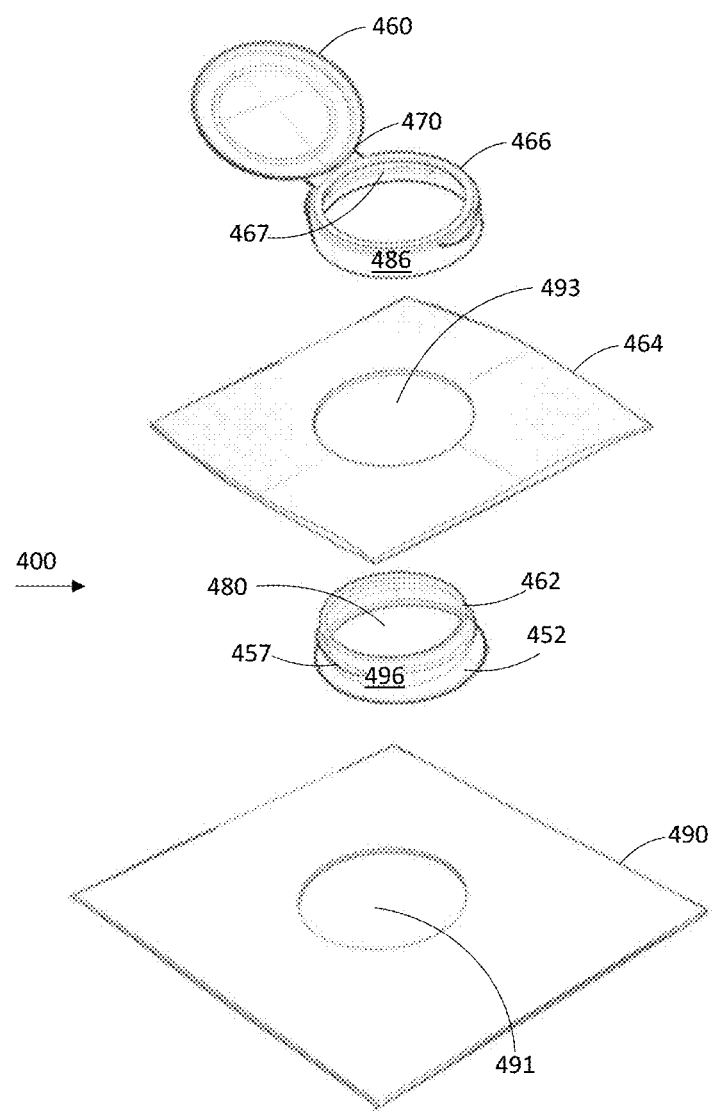
FIG. 7A is an exploded view of another embodiment of an exemplary fillable device, which contains a top portion and a bottom portion. The top portion contains a cap that is hingedly connected to the side wall of the top portion and is able to open and close using the hinge. The top portion attaches to the bottom portion via mating threads and thereby forms the compartment of the device. The fillable device also includes a flexible absorbent material, such as a foam pad, sandwiched between the top portion and the bottom portion.

Optionally, the device includes a flange at the base of the compartment (see, e.g., FIG. 4B, 152; FIG. 5, 152'; FIG. 7A, 452; FIG. 9F, 652). The flange may be formed of a material that is more flexible than the side wall of the compartment. In some embodiments, the flange attaches to the front side of the flexible material or a flexible sealant that attaches to the front side of the flexible material. In these embodiments, the surface of the flange that attaches to flexible material or flexible sealant typically contains an adhesive, such as any one of those described in the adhesive section (i.e., section D) below. In some embodiments, the flange attaches to the back side of the flexible material. The adhesive that attaches the flange to the back side of the flexible material may be the same as the adhesive that attaches the device to a patient's skin. Alternatively, a second, different adhesive is incorporated on an attachment portion (see, e.g., FIG. 9F, 638) on the back side of the flexible material, where the attachment portion has a suitable size and shape for attaching the flange to the flexible material. The second adhesive can be formed from any suitable material, such as a rubber-based adhesive or an adhesive that is stronger than the adhesive that attaches the device to the patient's skin.

The attachment portion and the flexible material may be a unitary piece or two separate pieces that attach to each other. When the attachment portion and the flexible material are two separate pieces, a first surface of the attachment portion typically adheres to the back side of the flexible material, and a second, opposing surface of the attachment portion adheres to the flange. For example, the attachment portion is formed from a double-coated and conformable PET film with a rubber-based adhesive on both sides, such as MED 8345 (Avery Dennison) that contains a rubber-based adhesive on two opposing surfaces; while the flexible material is formed from a single-coated, highly conformable, thin polyethylene foam with an acrylic adhesive, such as MED 5637 (Avery Dennison) that contains an acrylic adhesive on the back side of the flexible material. Accordingly, a first adhesive surface of the attachment portion attaches to the back side of the flexible material and a second, opposing adhesive surface attaches to the flange. The flange surrounds the side wall of the compartment to provide additional support to the device, thereby facilitate attachment to and removal of the device from the patient's skin. The flange can also help form a seal surrounding the opening of the compartment, in particular when the flange attaches to the adhesive on the back side of the flexible material (see, e.g., FIGS. 9D and 9E).

The flange can have any suitable shape defined by a compartment border (see, e.g., FIG. 9C, 687) and an edge border (see, e.g., FIG. 9C, 689), as long as it forms a seal surrounding the opening of the compartment. For example, the flange has a circular shape surrounding the side wall of the compartment (see, e.g., FIG. 4B, 152). The compartment border (see, e.g., FIG. 4D, 187) aligns with the border of a circular through hole (see, e.g., FIG. 4D, 191) of the flexible material, such that when the flange is attached to the front or back side of the flexible material, a seal is formed surrounding the opening of the compartment (see, e.g., FIG. 4E).

In some embodiments, the circular flange contains a cut-out, forming a connecting portion on the flange (see, e.g., FIG. 9E, a u-shaped cut-out on the flange forms a connecting portion 630). In these embodiments, the connecting portion of the flange (see, e.g., FIG. 9E, 630) and the opening of the compartment (see, e.g., FIG. 9E, 614), together, align with the through hole (see, e.g., FIG. 9F, 691) of the flexible material, such that when the flange is attached to the front or back side of the flexible material, the opening of the compartment at least partially aligns with the through hole and a seal is formed surrounding the opening of the compartment (see, e.g., FIG. 9E).

When applied on the patient's skin over the port site, the compartment border of the flange (see, e.g., FIG. 9E, 687) conforms to the surface of the patient's skin, forming a seal to prevent medication inside the compartment from spreading to areas of the patient's skin located outside of the port site.

2. Sealant Material

Optionally, a sealant material, such as a woven pad or foam material, is located between the compartment and the flexible material. In embodiments of a compartment formed by a top portion and a bottom portion, such as a flange, a flexible sealant is located between the top portion and the bottom portion (see, e.g., FIG. 7A-7B). The sealant has a first side facing toward the top of the compartment and an opposite, second side, which typically contains an adhesive coating or is attached to the front side of the flexible material via an adhesive. The second side of the sealant attaches to the front side of the flexible material using the adhesive coating. The sealant included in the device has a suitable size, shape, and thickness to provide structural support to the compartment and/or prevent leakage of the medication from inside of the Compartment. The sealant included in the device contains a through hole that has a suitable shape and dimensions sufficient to align with the opening in the compartment and provide a seal surrounding the opening of the compartment.

For example, as shown in FIG. 7A, a sealant material can be in the form of a foam pad 464 which contains a second through hole 493 in the device 400, through which the top portion 466 is screwed on the bottom portion 462, and thereby form a seal surrounding the opening 480 of the compartment. The second through hole 493 of the sealant material aligns with the opening 480 of the compartment and the through hole 491 of the flexible material.

When one or more sealant materials are included in the device, the sealant material can be a foam material, such as closed-cell ethylene-vinyl acetate, closed-cell polyethylene, silicone, rubber, urethane, or those sold under Avery Dennison Medical, for example, Avery Dennison MED 5645, or other compressible materials. The adhesive coating on the second side of the sealant material can be any of the adhesives described below for the flexible material, such as an acrylic adhesive suitable for medical applications. When more than one sealant material is included in the device, each sealant material can be the same as or different from the other(s).

The specific shape, size, and thickness of the sealant material included in the device depends on the shape and dimensions of the compartment and flexible material, the formulation being applied, as well as the port site of the patient. For example, the sealant material included in the device has the shape of a square, a rectangle, or a circle. Typically, the overall size of the sealant material is smaller than the overall size of the flexible material.

Typical thicknesses of the sealant material range from about 50 µm to about 1 cm, from about 100 µm to about 800 µm, from about 200 µm to about 700 µm, or from about 300 µm to about 600 µm, from about 400 µm to about 550 µm, such as about 500-515 µm. When the sealant material has the shape of a square, the length of the square can be in a range from about 2 cm to about 15 cm, from about 2 cm to about 10 cm, or from about 2 cm to about 8 cm. When the sealant material has the shape of a rectangle, the length of the rectangular can be in a range from about 3 cm to about 15 cm, from about 4 cm to about 12 cm, or from about 5 cm to about 15 cm; the width of the rectangular can be in a range from about 1 cm to about 12 cm, from about 2 cm to about 10 cm, or from about 3 cm to about 8 cm. When the sealant material has the shape of a circle, the diameter of the circle can be in a range from about 4 cm to about 15 cm, from about 4 cm to about 12 cm, or from about 5 cm to about 12 cm.

3. Cushion Material

Optionally, a cushion material, such as a foam pad or a woven pad (e.g. a gauze pad), is located between the compartment and the flexible material and/or on the back side of the flexible material surrounding the through hole of the flexible material to provide comfort at the contact point between the device and the patient's skin. The cushion material can have any suitable shape and size as long as it can provide additional comfort to the user, such as a foam pad in the form of an O-ring, a rectangle, a square, etc. The cushion material contains a though hole, having a shape and dimensions sufficient to align with the opening of the compartment and/or the through hole of the flexible material. In embodiments in which the cushion material is located on the back side of the flexible material, when in use, the cushion material is in direct contact with the patient's skin, and thereby provides a region that absorbs and dissipates the anesthetic over the subdermal port prior to injection; acts as a barrier to bacteria from entering wounds; retains moisture; and/or promotes healing.

Figure 7B:
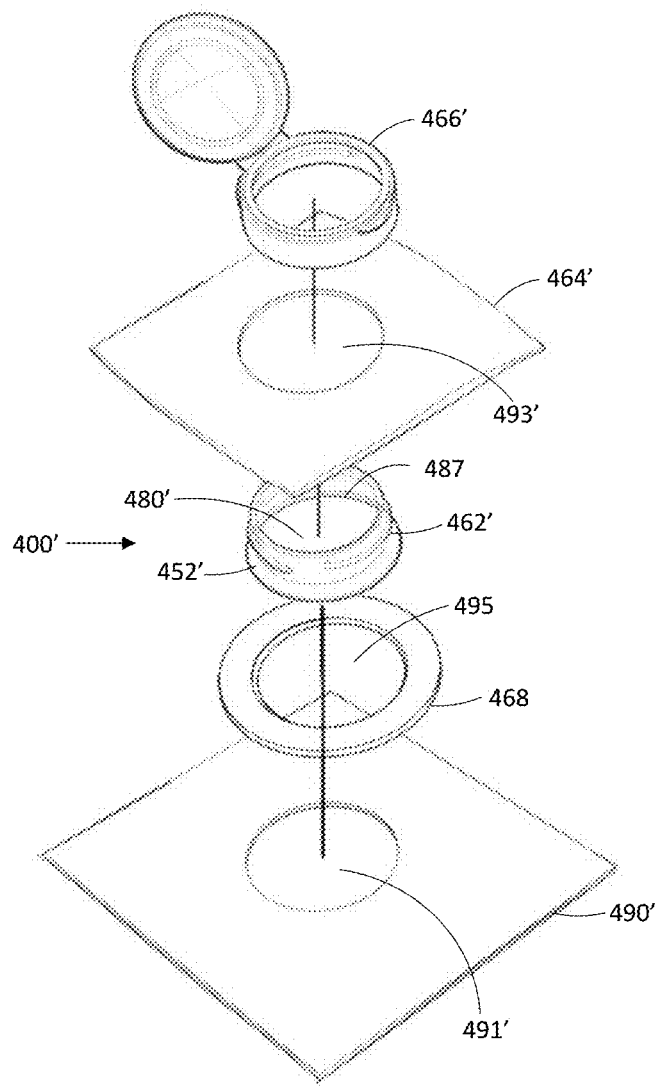
FIG. 7B is an exploded view of another exemplary device, which is similar to the device of FIG. 7A, and includes a cushion material to provide additional comfort to the user, such as a foam pad in the form of an O-ring, at the base of the bottom portion.

For example, as shown in FIG. 7B, a cushion material, such as a foam pad 468 in the form of an O-ring, is located between the bottom portion and the flexible material to reduce the contact pressure from the border of the compartment when applied on the patient's skin. The cushion material contains a third through hole 495 in the device 400', which aligns with the through hole 491' of the flexible material, the opening 480' of the compartment, and the second through hole 493' *of* the flexible sealant. Optionally, the dimensions of the third through hole 495 in the foam pad are sufficient to allow the entire opening of the compartment to be exposed on the back side of the device, upon removal of the protective layer.

C. Flexible Material

The flexible material surrounding the compartment is a piece separate from the compartment or connects to the compartment as part of a unitary piece. The flexible material may be a fabric material or plastic, coated on one side with an adhesive layer. Exemplary flexible materials include woven fabrics, plastics (such as acrylic, polyvinyl chloride, polyethylene, polypropylene (e.g. high density polypropylene and low density polypropylene), polyurethane, silicone rubber, etc.), and latex strips. Optionally, the material is waterproof. Optionally the flexible material is formed of materials for use with sensitive skin. For example, the material can be a High Moisture Vapor Transmission Rate film, such as in the Smith & Nephew IV3000 transparent dressing, OTS bandages, Avery Dennison Medical, such as Silicone Tape Medical 5500 Double-Coated, or Trilaminate TPU Film with a High Tack Soft Silicone Adhesive from Avery Dennison Medical, MED 5637, or MED 8345, or a combination thereof.

The flexible material maybe formed from a single type of material, such as any one of those described above, for example, a single-coated, highly conformable, thin polyethylene foam with an acrylic adhesive, such as MED 5637 (Avery Dennison), or a combination of two or more different types of materials, such as a single-coated, highly conformable, thin polyethylene foam with an acrylic adhesive and a double-coated and conformable PET film with a rubber-based adhesive on both sides, e.g., MED 5637 and MED 8345.

In some forms, the flexible material contains an attachment portion on the front or back side of the flexible material (see, e.g., FIG. 9F, 638). The attachment portion of the flexible material is positioned surrounding at least a portion of the opening of the flexible material, and has a suitable size and shape for attaching the compartment, in particular via a flange of the compartment, to the flexible material. Typically, the attachment portion of the flexible material contains an adhesive that may be the same as or different from the adhesive that attaches the device to a patient's skin. For example, a first adhesive is incorporated on the back side of the flexible material that attaches the device to a patient's skin; and a second, different adhesive is incorporated on an attachment portion on the front or back side of the flexible material, where the attachment portion has a suitable size and shape for attaching a flange of the compartment to the flexible material. The second adhesive can be formed from any suitable material, such as a rubber-based adhesive or an adhesive that is stronger than the adhesive that attaches the device to the patient's skin.

The attachment portion of the flexible material may be formed using a unitary piece together with the flexible material or a separate piece that attach to the flexible material. When the attachment portion is formed from a separate piece, a first surface of the attachment portion typically adheres to the front or back side of the flexible material, and a second, opposing surface of the attachment portion adheres to the flange. For example, the attachment portion is formed from a double-coated and conformable PET film with a rubber-based adhesive on both sides, such as MED 8345 (Avery Dennison) that contains a rubber-based adhesive on two opposing surfaces; while the flexible material is formed from a single-coated, highly conformable, thin polyethylene foam with an acrylic adhesive, such as MED 5637 (Avery Dennison) that contains an acrylic adhesive on the back side of the flexible material. Accordingly, a first adhesive surface of the attachment portion attaches to the back side of the flexible material and a second, opposing adhesive surface attaches to the flange. See, for example, flexible material 690 shown in FIGS. 9A-9F, where the flexible material 690 is formed by MED 5637 and thus contains an acrylic adhesive 610, while the attachment portion 638 is formed by MED 8345 and thus contains a rubber-based adhesive.

The flexible material contains a through hole defined by a front border and a back border. The through hole of the flexible material aligns with at least a portion of the opening of the compartment. The through hole can have any suitable shape, such as a square, triangle, diamond shape, rectangle, circle, and other regular and irregular shapes, as long as it aligns with at least a portion of the opening of the compartment to allow the opening to expose to the patient skin when in use. For examples, the through hole has a circular shape with a diameter ranging from about 1 inch to about 2 inches, from about 1 inch to about 1.5 inches in diameter, from about 1 inch to 1.4 inches, from about 1 inch to about 1.3 inches, or from about 1 inch to about 1.2 inches, such as for example about 1.1 inch or about 1.5 inches.

In some forms, the through hole of the flexible material is generally circular in shape and also contains a cut-out portion, such as a u-shaped cut-out portion (see, e.g., FIG. 9F, a u-shaped cut-out portion 639). Typically, the cut-out portion is configured to permit the hinge to pivot over a range of about 90' from an open position to a closed position and thereby move the cap and side wall of the compartment from an open position to a closed position, and/or vice versa. When the through hole of the flexible material contains a cut-out portion (see, e.g., FIG. 9F, 639), the flange of the compartment may contain a connection portion that has a shape and size corresponding to the shape and size of the cut-out portion of the through hole (see, e.g., FIG. 9F, 630), such that when the flange is attached to the front or back side of the flexible material, the connecting portion of the flange aligns with and forms a seal on the cut-out portion of the through hole and the opening of the compartment at least partially aligns with the circular portion of the through hole (see, e.g., FIG. 9E). When applied over the port site of the patient, the back side of the flexible material adhere to the patient's skin via an adhesive coating and the back border of the flexible material conforms to the patient's skin and thereby provides a tight seal between the back side of the flexible material and the skin to which it contacts. Such tight seal prevents leakage of the medication from inside of the compartment.

In some embodiments, the flexible material is a plastic that has sufficient rigidity to support the compartment and provide a tight seal between the back side of the flexible material and the contact skin. When the flexible material is a rigid plastic, such as polypropylene, polyethylene (e.g., high density polyethylene), acrylic, polyurethane, or silicone rubber, the compartment can connect to the flexible material by mechanical assembly, such as by mechanically pressing the compartment and flexible material together. A portion of the compartment connects to a portion of the flexible material with a tight fit such that no gap is present at the connection portion of the assembled device to prevent leakage of medication from inside of the compartment. In some embodiments, the compartment contains a connecting portion and the flexible material contains a corresponding receiving portion. The connecting portion is configured to mate with and be received by the receiving portion, such as by having protrusions on the receiving portion that align with and fit in corresponding grooves on the connecting portion, or vice versa. For example, as shown in FIGS. 8A-8D, the compartment contains a cap 560 connected to a portion 554 of the side wall via a hinge 570, where the cap 560 opens and closes via the hinge 570. The interior surface 552 of the side wall 550 contains a connecting portion 556. The flexible material 590 contains a receiving portion 592 that is raised relative to the front side 540 of the flexible material 590. The compartment 514 connects to the flexible material 590 by aligning and mechanically pressing together the connecting portion 556 of the compartment and the receiving portion 592 of the flexible portion with a tight fit, such that a seal is formed at the connection portion 530 of the device. In these embodiments, the border 587 of the compartment fits tightly surrounding the base of the receiving portion. When applied to the patient's skin, the back border 599 of the through hole 591 on the back side of the device conforms to the surface of the patient's skin forming a seal to keep the medication in contact with port site (via the through hole of the flexible material that aligns with the opening of the compartment) and prevent it from spreading to areas of the patient's skin located outside of the port site.

The flexible material can be a polymer film, such as polypropylene; polyethylene, such as low density polyethylene, linear low density polyethylene, metallocene polyethylene and high density polyethylene; polyvinyl chloride; polyester (e.g. polyethylene terephthalate); polyvinylidene chloride; ethylene vinyl acetate (EVA) copolymer; polyurethane; cellulose acetate. Optionally, the polymer film is a coextruded multilayer polymer film.

The flexible material can be formed from polyethylene, a polyethylene blend, polyethylene composite, or a polyurethane.

Optionally additives, such as a tackifier, a plasticizer, a coloring agent, and/or an antioxidant are included to form the polymer film.

The flexible material can have any suitable shape and dimension to allow placement of the device on the skin in the desired site. For example, the flexible material of the device has a shape of a square, a rectangle, or a circle, or other regular shapes or irregular shapes. In some embodiments, the flexible material of the device has a regular shape with irregular edges, for example, a square or rectangular shape with rounded (inverted or everted) corners or edged corners, a square or rectangular shape with wavy edges, etc. Typical thicknesses range from about 20 µm to about 1.5 mm, from about 30 µm to about 1.2 mm, from about 40 µm to about 1.0 mm, from about 50 µm to about 1.0 mm, from about 80 µm to about 0.9 mm, from about 20 µm to about 0.5 mm, from about 20 µm to about 0.25 mm, or from about 20 µm to about 0.1 mm, such as about 40 µm, about 80 µm, about 0.2 mm, or about 0.9 mm. When the flexible material has the shape of a square, the length of the square can be in a range from about 5.5 cm to about 15 cm, from about 5.5 cm to about 12 cm, from about 5.5 cm to about 10 cm, or from about 5.5 cm to about 8 cm, such as about 5.5 cm or about 7.5 cm. When the flexible material has the shape of a rectangle, the length of the rectangular can be in a range from about 8 cm to about 15 cm, from about 8 cm to about 14 cm, or from about 8 cm to about 12 cm; the width of the rectangular can be in a range from about 5.5 cm to about 12 cm, from about 6 cm to about 12 cm, or from about 7.5 cm to about 11.5 cm, such as a rectangular foam material having a length of about 10 cm and a width of about 7.5 cm. When the flexible material has the shape of a circle, the diameter of the circle can be in a range from about 5.5 cm to about 15 cm, from about 5.5 cm to about 12 cm, or from about 5.5 cm to about 10 cm.

D. Adhesive Layer

The adhesive coating on the back side of the flexible material may contain any medically compatible adhesive that is suitable for topical application to human skin. The adhesive is generally a pressure sensitive adhesive that can adhere to human skin firmly and releasably. The adhesive may contain one or more acrylates, such as methacrylates and/or epoxy diacrylates (also referred to as vinyl resins).

Examples of suitable adhesives include acrylates, silicones, polyisobutylenes, synthetic rubbers, natural rubbers, copolymers and mixtures thereof. Acrylate and silicone can be suitable adhesives. In general, the adhesive produces little or no occurrence of skin irritation or sensitization when applied to the skin site for up to about 1 to 2 hours.

The adhesive may be a suitable pressure sensitive adhesive for use on sensitive skin, such as the adhesive in Smith & Nephew IV3000 transparent dressing.

The adhesive may be an acrylic acid (or methacrylic acid) copolymer. The copolymer can include one or more main monomers and optionally one or more polar comonomers. Suitable main monomers for use include alkyl acrylates containing 4 to 12 carbon atoms in the alkyl group and alkyl methacrylates containing 4 to 12 carbon atoms in the alkyl group. Examples of suitable alkyl acrylates and methacrylates include n-butyl, n-pentyl, n-hexyl, isoheptyl, n-nonyl, n-decyl, isohexyl, 2-ethyloctyl, isooctyl and 2-ethylhexyl acrylate and methacrylate. In some embodiments, alkyl acrylates may include isooctyl acrylate, 2-ethylhexyl acrylate, n-butyl acrylate, and cyclohexyl acrylate. Suitable polar monomers include monomers having hydroxyl, amide or carboxylic acid, sulfonic acid or phosphonic acid functionalities. Representative examples include acrylamide, methacrylamide, N-vinyl 2-pyrrolidone, 2-hydroxyethyl acrylate, 2-hydroxyethyl methacrylate, hydroxypropyl acrylate, acrylic acid, methacrylic acid, pyrrolidonylethyl acrylate, and alkoxyethyl acrylate (e.g. 2-carboxyethyl acrylate). Optionally, the polar monomer weight is up to than 40% of the total weight of all the monomers forming the copolymer. For example, the polar monomer(s) may be incorporated in the copolymer in a concentration of about 1% to about 20% by weight.

The acrylate copolymer may comprise a reaction product of a polar monomer that is the main monomer and an additional optional monomer, which, if present, is non-adhesive to the adhesive composition. The amount that does not become viscous is included in the polymerization reaction. Optional additional monomers may be added for other purposes, for example to improve performance, reduce costs, or for other purposes. Examples of such optional monomers include vinyl esters such as vinyl acetate, vinyl chloride, vinylidene chloride, styrene, and macromonomers that are copolymerizable with other monomers. Suitable macromonomers include polymethyl methacrylate, styrene/acrylonitrile copolymers, polyethers, and polystyrene macromonomers.

The adhesive can be any adhesive material suitable for use on skin of a patient, such as a silicone or polysiloxane pressure sensitive adhesive. Exemplary suitable silicone pressure sensitive adhesives that are commercially available include, but are not limited to, silicone adhesives sold under the trademark BIO-PSA® by Dow Corning Corporation, Medical Products, Midland, Michigan, OTS bandages, and Avery Dennison Medical, such as Silicone Tape Medical 5500 Double-Coated and Trilaminate TPU Film with a High Tack Soft Silicone Adhesive from Avery Dennison Medical, single-coated or double-coated conformable polyethylene foam materials and PET films, such a single-coated, highly conformable, thin polyethylene foam with an acrylic adhesive, such as MED 5637 (Avery Dennison), and double-coated and conformable PET film with a rubber-based adhesive on both sides, such as MED 8345 (Avery Dennison), and combinations thereof.

E. Formulations

The device may be prefilled or filled at the time of use with one or more topical formulations, such as local anesthetics in a form suitable to topical application. Examples of suitable local anesthetics include lidocaine, lidocaine hydrochloride, prilocaine, etidocaine, bupivacaine, procaine, benzocaine, tetracaine, ethyl aminobenzoate, procaine hydrochloride, dibucaine, dibucaine hydrochloride, tetracaine hydrochloride, and diethyl aminoethyl p-butylamino-benzoate hydrochloride, or a combination thereof. In some embodiments the medication contains lidocaine. Optionally the medication contains two or more local anesthetics, such as, for example, lidocaine and tetracaine, or lidocaine and prilocaine. For example, the formation is an Emla cream that contains lidocaine and prilocaine.

The terms medication and formulation are generally used interchangeably herein. The medication is in a form suitable for topical delivery, such as a lotion, cream, or gel, optionally the medication is in the form of a cream.

Optionally the topical formulation contains one or more additional active agents, such as antibiotics.

F. Removable Protective Layer

The removable protective layer prevents the adhesive layer from adhering to any packaging material (e.g. an envelope) or to itself.

The protective layer can include a first side and a second side, located opposite each other. The first side contacts the adhesive layer on the back side of the device, and the second side faces outward from the device and is located opposite the first side.

In embodiments of the device containing a prefilled compartment, the second side of the protective layer is also in contact with the removable layer that covers the opening to the compartment.

The protective layer may be formed from any material that facilitates its release from the adhesive layer. For example, the protective layer can be polyvinyl chloride, or any other synthetic resin. The protective layer may also be provided at one end with a slit or a tab which facilitates its removal.

The protective layer can optionally be craft paper, polyethylene, polypropylene, polyester or composites of any of these materials.

The protective layer can be coated with release agents, such as fluorochemicals or silicones. The protective layers can be papers, polyolefin films, or polyester films coated with silicone release materials.

G. Optional Features

Logos, messages, such as inspirational messages, or other pleasing designs may be provided on the front side and/or the removable protective layer.

Optionally, each device is packaged separately from other devices in packaging material. Optionally a group of two or more devices, such as up to 20, up to 15, up to 10, or up to 5 devices, is packaged together in packaging material. For example, the packaging material can be a sealed envelope-like package, a cardboard box, or a plastic box.

H. Exemplary Devices

1. Pre-Filled Devices

Exemplary pre-filled devices are illustrated in FIGS. 1A-1D.

As shown in FIG. 1A, the device 100 contains a flexible material with an adhesive coating 110 and an inert compartment 114 containing a local anesthetic 112 in a form suitable for topical administration.

Figure 1B:
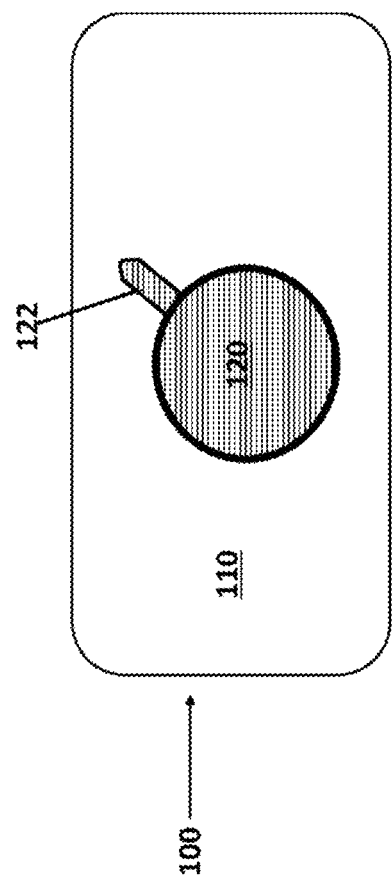

As shown in FIG. 1B, prior to use, the opening of the compartment is covered with a removable layer 120 to retain the medication in the compartment and keep it sterile. The removable layer may include a tab portion 122 to facilitate pulling the layer to remove it. The tab portion typically extends beyond the perimeter of the opening to the compartment. Optionally the removable layer is coated paper or foil material. The removable layer is typically a water-impermeable material or contains a water-impermeable coating on the side of the material that is in contact with the medication. In some embodiments, the removable layer 120 is a material as described above that can break open upon application of a pressure by a user to release the medication in the compartment.

As shown in FIG. 1C, when fully assembled, prior to use, the adhesive layer 110 is typically covered with a removable protective layer 132. The protective layer can be formed from one continuous material or two or more parts (132a, 132b). A portion of the protective layer is adjacent to and covers the removable layer 120 which covers the opening of the pre-filled compartment. Thus, prior to use, when fully assembled, a cross-sectional view of the pre-filled compartment contains the following layers: the top, outer layer contains the removable, protective layer 132, which covers the removable layer 120 (e.g. foil-layer or other water-impermeable layer), which is adjacent to and covers the medication 112, which is contained within the flexible, inert compartment 114 (see FIG. 1D).

2. Devices to be Filled with Medication after Application to the Patient's Skin

Exemplary devices to be filled after application to a patient's body are illustrated in FIGS. 2A-2C, 4A-4E, 5A-5B, 6, 7A-7B, 8A-8D, and 9A-9F.

As shown in FIG. 2A, the device 100' contains a flexible material with an adhesive coating 110' on the back side of the material and an empty inert compartment 114'. The compartment is surrounded by the flexible material with the adhesive coating. As shown in FIG. 2A, the compartment contains inlet opening 116 configured to receive the medication for topical administration and thereby fill the compartment with the medication.

As shown in FIG. 2B, the front side 140 of the flexible material of the device 100' includes an inlet connector 118, which is configured to mate with the outlet 218 of a container 210 containing the medication to be administered to the patient. The inlet connector 118 includes an inlet opening 116 which connects to the inside of the compartment 114'. When the container 210 containing the medication is connected to the inlet connector 118 and the medication is squeezed or pushed out of the container, it enters the compartment of the device via the inlet opening 116. Optionally, the inlet opening contains a one-way valve or is a self-sealing opening. Typically, the compartment, the inlet connector, and the inlet opening are formed from silicon.

Figure 2C:
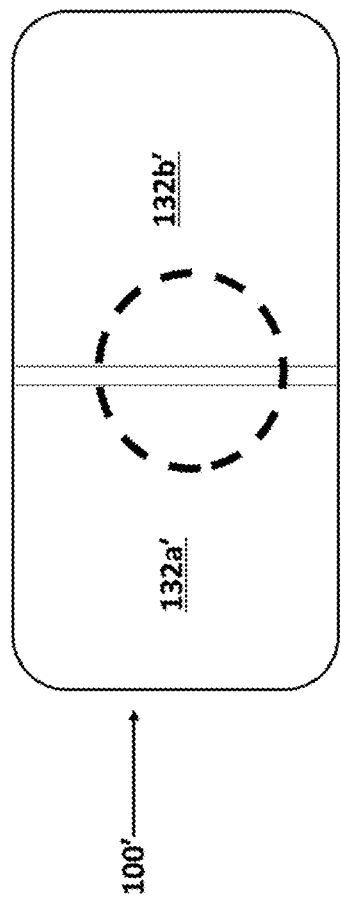
Figure 3:
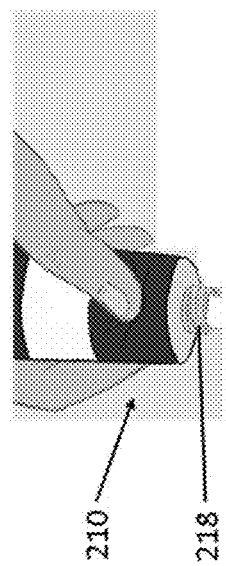
FIG. 3 illustrates an exemplary container containing a topical medication being squeezed out of the outlet of the container.

As shown in FIG. 2C, when fully assembled, prior to use, the adhesive layer 110' is typically covered with a removable protective layer 132'. The protective layer can be formed from one continuous material or two or more parts (132a', 132b').

As shown in FIG. 4A, the device 100" contains a compartment 114" and a flexible material 190. The compartment is defined by a circular side wall 150 and a cap 160 and attaches to the front side 140" of the flexible material, where the cap 160 is in the closed position. As shown in FIG. 4B, the cap 160 is connected with a portion of the side wall 150 via a hinge 170, such that the cap opens and closes via the hinge 170. Optionally, the compartment includes a flange 152 sited at the base of the compartment. The flange 152 attaches to the front side 140" of the flexible material 190 and surrounds the side wall 150 of the compartment to provide additional support to the device. As shown in FIG. 4C, the compartment 114" of the device 100" contains an opening 180, which has a shape and dimensions corresponding to the shape and dimensions of a through hole 191 of the flexible material 190. As shown in FIG. 4D, the border 187 of the compartment aligns with the front border 197 of the through hole, and accordingly, the opening 180 of the compartment aligns with the through hole 191 of the flexible material. As shown in FIG. 4E, upon removal of a protective layer, the opening 180 is exposed (via the through hole) on the back side 142 of the device 100". After the device is applied to the port site of the patient, the back border 199 of the through hole 191 of the flexible material conforms to the surface of the skin and thereby forms a seal. The cap 160 is flipped open, and the medication is transferred into the compartment. The cap is then closed to contain the medication in the compartment. The medication inside the compartment is in direct contact with the skin via the opening of the compartment and the through hole. The seal formed by conforming the border of the though hole to the skin surface prevents leakage of the medication from inside of the compartment when in use.

As shown in FIG. 5, the device 100''' includes a removable cap 160', a bottom portion 162, optionally with a flange 152', and a flexible material 190'. The bottom portion 162 attaches to the flexible material 190', with its border 187' aligned with the front border 197' of the flexible material

190'. The cap 160' attaches to the device by being screwed on via threads (not shown on figure) on the cap that mate with corresponding threads 157 on the bottom portion 162. When the cap is screwed on the bottom portion, these two parts form the compartment of the device 100'''.

As shown in FIG. 6, the device 300 includes a sealant material in the form of a foam pad 364, located between the compartment 314 and the flexible material 390. Optionally, the foam pad 364 contains an adhesive coating (not visible) on the side that is in contact with the front side 340 of the flexible material 390 and attaches thereto. The foam pad 364 contains a second through hole 393, which has a shape and dimensions corresponding to the opening 380 of the compartment and the through hole 391 of the flexible material. The opening 380 of the compartment, second through hole 393 of the foam pad, and through hole 391 of the flexible material align with each other. As such, the foam pad 364 provides a seal surrounding the opening 380 of the compartment, when the device is applied to the skin.

Upon removal of a protective layer, the opening 380 is exposed on the back side of the device. After the device 300 is applied to the port site of the patient, the opening 380 is exposed to the patient's skin via the through holes 393 and 391 of the sealant and the flexible material. The back border 399 forms a seal between the through holes in the device and the patient's skin. The cap is flipped open along the hinge 370 that connects the cap to a portion of the side wall 350, and a medication is inserted into the compartment. The cap is then flipped into a closed position. While the device is in the closed position, the medication is in direct contact with the patient's skin, and the medication is prevented from leaking out of the inside of the compartment.

As shown in FIG. 7A, the device 400 includes a top portion 466, a bottom portion 462, optionally the bottom portion includes a flange 452, a flexible material 490, and a sealant material 464, such as in the form of a foam pad. Optionally, the device depicted in 7A does not include a sealant material 464. The bottom portion 462 is proximal to the flexible material 490. The top portion 466 contains a cap 460, which is connected with a portion of the top side wall 486 of the top portion via a hinge 470. The bottom portion 462 contains a bottom side wall 496 and the opening 480, and optionally a flange 452 at its base. The top portion 466 attaches to the bottom portion 462 by being screwed on using mating threads 467 and 457 on the top portion and the bottom portion, respectively. When the top portion is attached to the bottom portion, the two parts form the compartment of the device 400, where the top side wall 486 of the top portion and the bottom side wall 496 of the bottom portion together form the side wall of the compartment.

The sealant material 464 contains a second through hole 493. The second through hole 493 has a circular shape and dimensions sufficient to allow the top portion 466 being screwed onto the bottom flange 462 through the second through hole 493. After the top portion attaches to the bottom portion, the sealant material 464 is sandwiched therebetween and thereby provides a seal surrounding the opening of the compartment of the device. The second through hole 493 aligns with the opening 480 of the compartment and the through hole 491 of the flexible material.

Figure 8B:
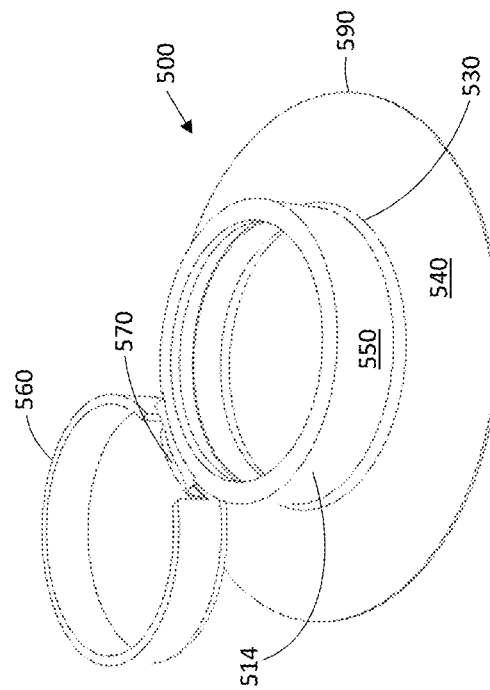
FIGS. 8A-8D are different views of another embodiment of an exemplary device that can be filled with the topical formulation after the device is applied to the patient's skin.
Figure 8A:
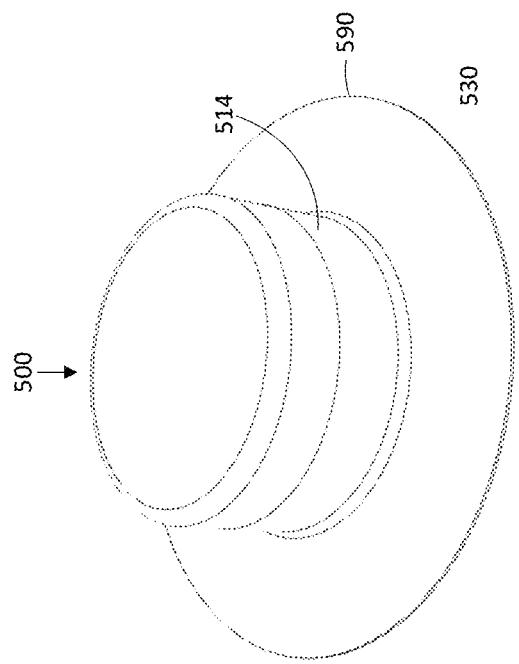
Figure 8D:
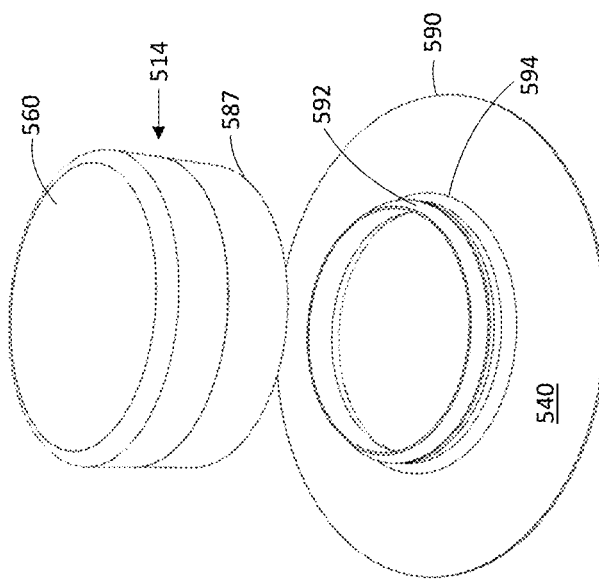
Figure 8C:
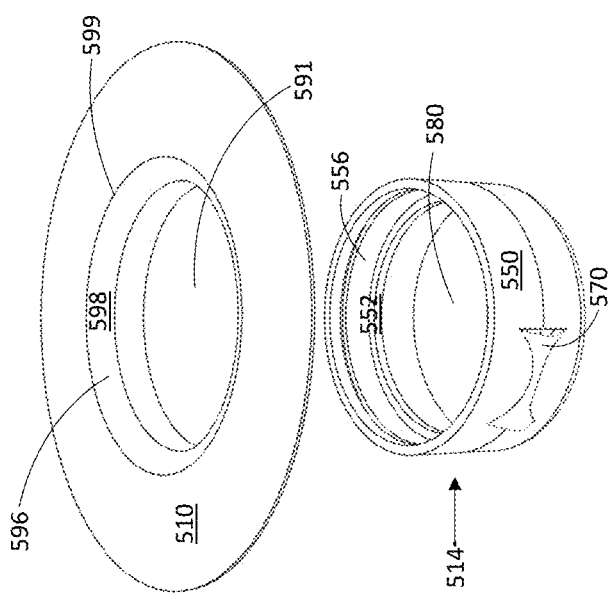

Optionally, a cushion material is included in the device, such as depicted in device 400' shown in FIG. 7B. As shown in FIG. 7B, the device 400' includes a sealant material 464', located between the top portion 466' and the bottom portion 462', optionally including a flange at its base, and a cushion material 468 located between the bottom portion 462' and the flexible material 490'. The cushion material 468 is in the form of an O-ring with a third through hole 495. The third through hole 495 has dimensions sufficient to support the border 487 of the opening 480 to reduce the contact pressure between the border 487 of the compartment and the patient's skin, when the device is in use. The third through hole 495 of the cushion material aligns with the through hole 491' of the flexible material, the opening 480' of the compartment, and the second through hole 493' of the flexible sealant. As shown in FIG. 8A, the device 500 includes a compartment 514 and a flexible material 590, which are mechanically connected via a connection portion 530. As shown in FIG. 8B, the compartment 514 is defined by a circular side wall 550 and a cap 560 on the front side 540 of the flexible material, where the cap 560 is in the open position. The cap 560 is connected with a portion of the side wall 550 via a hinge 570, such that the cap opens and closes via the hinge 570. As shown in FIGS. 8C, the interior surface 552 of the side wall 550 contains a connecting portion 556. As shown in FIG. 8D, the flexible material 590 contains a corresponding receiving portion 592 that is raised relative to the front side 540 of the flexible material 590. The connecting portion is configured to mate with and be received by the receiving portion, such as by having protrusions on the receiving portion that align with and fit in corresponding grooves on the connecting portion, or vice versa. The compartment 514 connects to the flexible material 590 by aligning and mechanically pressing together the connecting portion 556 of the compartment and the receiving portion 592 of the flexible portion with a tight fit, such that a seal is formed at the connection portion 530 of the device. In these embodiments, the border 587 of the compartment surrounds the base 594 of the receiving portion 592. The opening 580 of the compartment 514 aligns with the through hole 591 of the flexible material. Optionally, the flexible material includes a tapered portion 596 on the inside wall 598 of the receiving portion 592. The tapered portion can be configured to facilitate removal during manufacture, optionally when the flexible material and the receiving portion are formed by injection molding. An adhesive coating 510 is on the back side of the device. The adhesive coating may cover the entire back side of the flexible material or a portion of the back side of the flexible material.

Prior to use, the adhesive layer 510 is typically covered with a removable protective layer. When applied to the patient's skin, the back border 599 of the through hole of the flexible material on the back side of the device conforms to the surface of the patient's skin forming a seal to keep the medication in contact with port site (via the through hole of the flexible material that aligns with the opening of the compartment) and prevent it from spreading to areas of the patient's skin located outside of the port site.

As shown in FIG. 9A, the device 600 contains a compartment 614 and a flexible material 690. The compartment is defined by a circular side wall 650 and a cap 660, where the side wall is raised relative to the front side 640 of the flexible material, where the cap 660 is in the closed position. As shown in FIG. 4B, the cap 660 is connected with a portion of the side wall 650 via a hinge 670, such that the cap opens and closes via the hinge 670. The compartment 614 of the device 600 contains an opening 680, which aligns with a through hole of the flexible material 690.

Optionally, as shown in FIG. 9C and FIG. 9F, the compartment includes a flange 652 sited at the base of the compartment and surrounds the side wall 650 of the compartment. The flange 652 has a shape defined by a compartment border 687 and an edge border 689. A u-shaped cut-out on the flange forms a connecting portion 630. The flexible material 690 contains a through hole 691. The through hole 691 has a shape defined by a front border 697 and a back border 699. The through hole 691 is generally circular in shape and also contains a u-shaped cut-out portion 639, which is configured to permit the hinge to pivot over a range of about 90° from an open position to a closed position and thereby move the cap from an open position to a closed position, and/or vice versa. The front surface 658 (shown in FIG. 9C) of the flange 652 attaches to an attachment portion 638 on the back side of the flexible material 690. The attachment portion 638 may be formed from a piece that is separate from the flexible material. The attachment portion 638 may contain an adhesive that is the same as the adhesive 610 that attaches the device to the skin of a patient, or different from adhesive 610. For example, the flexible material 690 contains an acrylic adhesive 610, while the attachment portion 638 contains a rubber-based adhesive. For example, the flexible material 690 is formed by a single-coated, highly conformable, thin polyethylene foam with an acrylic adhesive 610, such as MED 5637, and thus contains an acrylic adhesive 610, while the attachment portion 638 is formed by MED 8345 and thus contains a rubber-based adhesive.

As shown in FIGS. 9E and 9F, the shape of the through hole 691 aligns with the opening 680 of the compartment, and the connecting portion 630 of the flange seals the cut-out portion 639 of the through hole of the flexible material 690, and the compartment border 687 of the flange aligns with the circular portion of border 699. Accordingly, the opening 680 of the compartment aligns with the through hole 691 (shown in FIG. 9F) of the flexible material 690, and a seal surrounding the opening 680 of the compartment is formed by the flange 652.

As shown in FIG. 9D, upon removal of a protective layer (not shown in FIG. 9D; illustrated in FIGS. 1C and 1D, 132) that covers the adhesive on the back side of the flexible material, the opening 680 of the compartment is exposed (via the through hole 691 of the flexible material) on the back side of the device. After the device is applied to the port site of the patient, the compartment border of the flange 687 conforms to the surface of the patient's skin and thereby forms a seal around the port site. As shown in FIG. 9E, when the cap 660 is flipped open, the medication can be inserted into the compartment. The cap can then be closed to contain the medication in the compartment and protect it from the ambient environment. The medication inside the compartment is in direct contact with the skin via the opening 680 of the compartment and the through hole 691 of the flexible material. The seal formed by conforming the border of the though hole to the skin surface prevents leakage of the medication from inside of the compartment when in use.

II. Kits

Optionally one or a plurality of the devices described herein is provided in a kit. The device or each device provided in the kit can be in any form of the devices described herein.

For embodiments in which the device is not prefilled with medication, optionally the kit also contains a container containing the topical medication therein. The inlet connector of the compartment is configured to mate with the outlet of the container containing the medication to be administered.

In some forms, a kit containing the device(s) also contains one or more applicators containing an antiseptic for cleaning the port site prior to application of the device and/or after the device is removed from the patient's skin.

III. Methods of Use

The devices and kits disclosed herein can be used by patients whenever a skin site is in need of a topically administered active agent, particularly the delivery of a local anesthetic. In particular, patients with implanted ports, such as an implanted chest port or a port implanted in the arm, can apply the devices described herein on top of their port site prior to intravenous delivery of medicine, vitamins, minerals (e.g. magnesium, calcium, zinc, etc.), electrolytes, or other nutrients, or a blood draw.

A. Types of Implanted Ports

The device can be used by patients who have any type of implanted port, such as a BardPort®, a Mediport®, a PowerPort®, Xcela Power Injectable Port®, or a Port-A-Cath®. The port can be single lumen or double lumen (also referred to as a dual lumen).

The implanted port can be a PowerPort. A PowerPort is a special type of port, available in single or double lumen, which can withstand higher injection pressures. The portal chamber is characterized by a triangular shape body, which can be palpated under the skin.

B. Method of Using Pre-Filled Device

To use the pre-filled devices described herein, the patient removes the paper backing from the adhesive layer. Next, the patient removes a protective foil layer, and thereby exposes the prefilled compartment.

Optionally, the port site is cleaned immediately prior to application of the device, such as by using an antiseptic. The port site can be cleaned using any suitable methods and tools, such as by using a cleaning device or instrument that is pre-filled with isopropyl alcohol or another suitable antiseptic, which is released at the time of use into a foam head or applicator and the applicator is applied to the port site. Suitable pre-filled cleaning devices include the BD ChloraPrep™ patient preoperative skin preparation and alcohol cleaning swabs (e.g., alcohol cleaning swabs from ID Enhancements Inc.), that are formed of a hollow plastic tube that serves as a handle and a foam head, where the antiseptic is stored inside the hollow plastic tube and is released into the foam head when a manual pressure is applied on the plastic tube, such as by squeezing the plastic tube. Optionally, the pre-filled cleaning device also contains one or more tabs attached to the hollow plastic tube, such that a user can apply a manual pressure on the tab(s) to release the antiseptic stored in the hollow tube.

The patient then places the opening to the prefilled compartment directly onto the site of the port and applies pressure to the adhesive layer surrounding the compartment so that the device adheres to the site of application.

Generally, the patient leaves the device over the port site for a sufficient period of time to numb the port site, typically about 10 minutes to an hour prior to chest port being accessed to deliver a medication, vitamins, minerals (e.g. magnesium, calcium, zinc, etc.), electrolytes, or other nutrients, or draw blood. During this time, the medication in the compartment is in contact with the port site.

Immediately prior to accessing the implanted port, the device is removed from the patient's skin and the port site is cleaned thoroughly, such as by using an antiseptic, to remove all cream residue. Any suitable methods and tools can be used for cleaning the port site, such as BD ChloraPrep™ patient preoperative skin preparation and alcohol cleaning swabs described above. The cleaned port site is allowed to dry prior to accessing the port. The removal step can be practiced by a healthcare professional, such as a nurse, or by the patient, or by another individual assisting the patient.

C. Method of Using a Fillable Device

To use the fillable devices described herein, the patient removes the paper backing from the adhesive layer. The patient then places the opening of the compartment directly onto the site of the port and applies pressure to the adhesive layer surrounding the compartment so that the device adheres to the site of application.

Optionally, the port site is cleaned immediately prior to application of the device, such as by applying an antiseptic. The port site can be cleaned using any suitable methods and tools, such as by using a cleaning device or instrument that is pre-filled with isopropyl alcohol or another suitable antiseptic, which is released at the time of use into a foam head or applicator and the applicator is applied to the port site. Suitable pre-filled cleaning devices include the BD ChloraPrep™ patient preoperative skin preparation and alcohol cleaning swabs (e.g., alcohol cleaning swabs from ID Enhancements Inc.), that are formed of a hollow plastic tube that serves as a handle and a foam head, where the antiseptic is stored inside the hollow plastic tube and is released into the foam head when a manual pressure is applied on the plastic tube, such as by squeezing the plastic tube. Optionally, the pre-filled cleaning device also contains one or more tabs attached to the hollow plastic tube, such that a user can apply a manual pressure on the tab(s) to release the antiseptic stored in the hollow tube.

In some embodiments, next, the patient attaches the outlet 218 of a container 210 containing the topical medication of interest, typically containing one or more local anesthetics, to the inlet connector 118 located on the compartment on the front side 140 of the flexible material. The patient then squeezes the container or otherwise pushes a sufficient volume of the medication out of the container, through the inlet opening 116 and into the inside of the compartment 114'.

In other embodiments, after placing a device on the patient's skin at the desired site, the cap is opened or removed, and a suitable volume of the medication and/or nutrient is placed inside the opening of the compartment of the device, in contact with the patient's skin. Then the cap is closed or reattached to the device.

For example, as shown in FIGS. 4A-4E, the device 100" can include a removable cap 160 that attaches to a portion of the side wall of the compartment via a hinge 170, such that it opens and closes using the hinge. The patient places the device 100" onto the site of the port as described above. The patient then flips open the cap 160 to provide access for the medication to be filled into the compartment. After a suitable amount of the medication is placed inside the compartment, the cap 160 is closed to contain the medication in the compartment. The medication inside the compartment is in direct contact with the skin through the opening of the compartment and the through hole of the flexible material.

Generally, the patient leaves the device over the port site for a sufficient period of time to numb the port site, typically about 10 minutes to an hour prior to chest port being accessed to deliver a medication or draw blood. During this time, the medication in the compartment is in contact with the port site.

Immediately prior to accessing the implanted port, the device is removed from the patient's skin and the port site is cleaned thoroughly, such as by using an antiseptic, to remove all cream residue. Any suitable methods and tools can be used for cleaning the port site, such as BD ChloraPrep™ patient preoperative skin preparation and alcohol cleaning swabs described above. The cleaned port site is allowed to dry prior to accessing the port. The removal step can be practiced by a healthcare professional, such as a nurse, or by the patient, or by another individual assisting the patient.

D. Time Period for Application

The patient applies the device to their skin such that the opening of the compartment is placed on top of the port site. Then the patient leaves the device on the site for a sufficient period of time to achieve analgesia in the skin at the port site. Typically, the patient leaves the device on the port site for about 10 to about 60 minutes prior to intravenous delivery of medicine or a blood draw through the port. For example, the patient may apply the device to port site at least 10 minutes, at least 15 minutes, at least 20 minutes, or at least 25 minutes, and up to about 60 minutes or up to about 30 minutes prior to intravenous delivery of medicine or vitamins, or a blood draw through the port. Optionally the device remains on the patient's skin, over the port site for 10 to 40 minutes, for 10 to 30 minutes, or for 10 to 20 minutes prior to intravenous delivery of medicine or a blood draw through the port.

The disclosed devices, kits, and methods can be further understood through the following numbered paragraphs.

1. A device for the topical delivery of local anesthetic to a port site comprising a front side and a back side, wherein the device comprises a compartment for containing a topical medication and a flexible material with an adhesive coating on one side, wherein the adhesive coating is on the back side of the device and wherein the opening for the compartment is on the back side of the device.
2. The device of paragraph 1, wherein the compartment does not contain an absorbent material.
3. The device of any one of paragraphs 1 to 2, further comprising a protective layer covering the adhesive coating on the back side of the device, optionally, wherein the protective layer also covers the opening for the compartment.
4. The device of any one of paragraphs 1 to 3, wherein the compartment is pre-filled with a medication in a form suitable for topical application comprising one or more local anesthetics.
5. The device of paragraph 4, wherein the medication comprises lidocaine.
6. The device of any one of paragraphs 4 to 5, wherein the back side of the device further comprises a removable layer covering the opening to the compartment, optionally the removable layer comprises a tab portion extending beyond the perimeter of the opening to the compartment.
7. The device of paragraph 6, wherein the protective layer covers the adhesive coating and the removable layer.
8. The device of paragraph 3 or paragraph 7, wherein the protective layer comprises two or more parts.
9. The device of any one of paragraphs 1 to 8, wherein the compartment is formed from silicon.
10. The device of any one of paragraphs 3 to 8, wherein the protective layer is a wax coated paper or plastic.
11. The device of any one of paragraphs 1 to 3, wherein the compartment comprises an inlet opening located on the front side of the device, wherein the inlet opening passes from the front side to the back side of the device.

12. The device of paragraph 11, wherein the inlet comprises an inlet connector located on the front side of the device, wherein the inlet connector is configured to mate with the outlet of a container containing the medication to be delivered.
13. The device of any one of paragraphs 1 to 12, where in the adhesive is a pressure sensitive adhesive.
14. The device of any one of paragraphs 1 to 13, wherein the flexible material and adhesive are suitable for application to sensitive skin.
15. A kit comprising the device of any one of paragraphs 1-3 or 8-12 and a container containing a topical medication.
16. The kit of paragraph 15 comprising a plurality of the devices.
17. The kit of paragraph 15 or paragraph 16, wherein the topical medication comprises one or more local anesthetics.
18. The kit of paragraph 17, wherein the medication comprises lidocaine.
19. A group of devices, comprising two or more devices of any one of paragraphs 1 to 14, in a packaging material.
20. The group of paragraph 19, comprising up to 20 devices, up to 15 devices, up to 10 devices, or up to 5 devices.
21. A method of delivering a local anesthetic to a skin site on a patient with an implanted port using the device of any one of paragraphs 1 to 14 comprising: placing the opening to the compartment onto the site of the port and applying pressure to the adhesive layer surrounding the compartment to adhere the device to the patient's skin.
22. The method of paragraph 21, wherein the device is the device of any one of paragraphs 1 to 3 or 8-14, and wherein the method further comprises attaching the outlet of a container containing the local anesthetic to the inlet connector on the front side of the device.
23. The method of paragraph 22, further comprising squeezing or pushing the local anesthetic out of the container and into the inlet opening and into the inside of the compartment.
24. The method of any one of paragraphs 21-23, wherein prior to the step of placing the opening of the compartment onto the site of the port, removing the protective layer from the adhesive.
25. The method of any one of paragraphs 21-24, wherein following the step of applying pressure to the adhesive layer, the device remains on the patient's skin for a sufficient period of time to numb the site, such as from about 10 minutes to about 1 hour.
26. The method of any one of paragraphs 21-24, further comprising, removing the device from the patient's skin and cleaning the skin site 10 minutes to 1 hour after the step of applying pressure to the adhesive layer.
27. The method of paragraph 24, wherein after the skin site is cleaned, the port is accessed via a needle.

The disclosed devices, kits, and methods can be further understood through the additional numbered paragraphs as follows.

1. A device for the topical delivery of a topical formulation, optionally a local anesthetic, to a port site comprising:
    a compartment configured to contain the topical formulation and a flexible material,
    wherein the compartment comprises a side wall, a top, and an opening that is opposite the top,
    wherein the flexible material comprises a front side, a back side, and a through hole,
    wherein the side wall of the compartment is raised relative to the front side of the flexible material,
    wherein a first adhesive coating is on the back side of the flexible material, and
    wherein at least a portion of the opening of the compartment aligns with the through hole of the flexible material.
2. The device of paragraph 1, wherein the compartment is attached to or integrated with the front side or the back side of the flexible material.
3. The device of paragraph 1, wherein the compartment comprises a flange, wherein the flange is attached to the front side or the back side of the flexible material, and optionally wherein the flange is attached to the back side of the flexible material.
4. The device of paragraph 3, wherein the flange comprises a connecting portion and the through hole of the flexible material comprises a cut-out portion, and wherein the connecting portion of the flange has a shape and size that corresponds with the shape and size of the cut-out portion of the through hole such that the connecting portion seals the cut-out portion.
5. The device of paragraph 3, wherein the flexible material comprises an attachment portion, wherein the flange is attached to the attachment portion of the flexible material, and optionally wherein the attachment portion surrounds at least a portion of the through hole of the flexible material.
6. The device of paragraph 5, wherein the attachment portion is a unitary piece with the rest of the flexible material or is a second, separate piece attached to a first piece forming the rest of the flexible material.
7. The device of paragraph 5, wherein a second adhesive coating is on the attachment portion of the flexible material, and wherein the adhesive forming the second adhesive coating is the same as or different from the adhesive forming the first adhesive coating.
8. The device of paragraph 5, wherein the attachment portion is on the back side of the flexible material, and wherein a front surface of the flange is attached to the attachment portion of the flexible material.
9. The device of paragraph 1, wherein the top is configured to be opened, allowing the topical formulation to be transferred into the compartment, and wherein the top is configured to be closed, allowing the topical formulation to be contained therein.
10. The device of paragraph 1, wherein the compartment is a unitary piece or formed by two or more separate parts.
11. The device of paragraph 10, wherein the top of the compartment is in the form of a cap, and wherein the cap is attached to a portion of the side wall of the compartment via a hinge and is able to open and close via the hinge.
12. The device of paragraph 10, wherein the top of the compartment is in the form of a cap, and wherein the cap is removable from the rest of the device.
13. The device of paragraph 12, wherein the compartment is formed by the cap and a bottom portion, wherein the bottom portion attaches to the front or back side of the flexible material, wherein the cap is removable from the bottom portion.

14. The device of paragraph 13, wherein each of the cap and the bottom portion comprises mating threads and the cap attaches to the bottom portion via the mating threads.

15. The device of paragraph 1, wherein the top of the compartment comprises an inlet connector configured to mate with the outlet of a container containing the topical formulation, and wherein the inlet connector comprises an inlet opening that connects to the inside of the compartment.

16. The device of paragraph 1, further comprising a protective layer covering the adhesive coating on the back side of the flexible material, and optionally wherein the protective layer also covers the through hole of the flexible material.

17. The device of paragraph 1, further comprising a removable layer, wherein the removable layer is located on the back side of the flexible material and covers the through hole of the flexible material to seal a local anesthetic contained inside the compartment, and
    optionally wherein the removable layer comprises a tab portion configured to facilitate pulling the removable layer off of the through hole, or the removable layer is formed from a material that breaks open upon application of a pressure by a user, to release the medication in the compartment.

18. The device of paragraph 1, wherein the device further comprises a flexible sealant optionally located between the compartment and the flexible material, wherein the flexible sealant comprises a second through hole, wherein the second through hole aligns with the opening of the compartment and the through hole of the flexible material; or
    wherein the device further comprises a cushion material optionally located between the compartment and the flexible material and/or on the back side of the flexible material, wherein the cushion material comprises a third through hole that aligns with the opening of the compartment and the through hole of the flexible material, or
    a combination thereof.

19. A kit comprising the device of paragraph 1, optionally a plurality of the device of paragraph 1, and a container containing a topical formulation, and optionally wherein the topical formulation comprises one or more local anesthetics.

20. A method of delivering a topical formulation, optionally wherein the topical formulation is a local anesthetic, to a skin site on a patient with an implanted port using the device of paragraph 1 comprising:
    placing the device onto the patient's skin such that the opening of the compartment is exposed to the site of the port via the through hole of the flexible material;
    applying pressure to the adhesive coating on the back side of the flexible material to adhere the device to the patient's skin; and
    optionally filling the compartment with the topical formulation through the top of the compartment.

I claim:

1. A device for the topical delivery of a topical formulation comprising one or more local anesthetics to an implanted port site on the skin of a patient, the device comprising:
    a flexible material and a compartment configured to contain the topical formulation,
    wherein the compartment comprises a side wall, a top, and an opening that is opposite the top, wherein the top is in the form of a cap,
    wherein the flexible material comprises a front side and a back side,
    wherein the compartment further comprises a flange extending from the side wall, the flange is attached to the back side of the flexible material, the flexible material surrounds the side wall, and the side wall extends beyond the front side of the flexible material,
    wherein an adhesive coating is on the back side of the flexible material configured to attach the device to the port site on the skin of the patient.

2. The device of claim 1, wherein the flexible material comprises an attachment portion on the back side of the flexible material, and wherein the flange is attached to the attachment portion of the flexible material.

3. The device of claim 2, wherein the attachment portion is a unitary piece with the rest of the flexible material or is a second, separate piece attached to a first piece forming the rest of the flexible material.

4. The device of claim 2, wherein a second adhesive coating is on the attachment portion of the flexible material, and wherein the second adhesive coating is the same as or different from the adhesive coating.

5. The device of claim 1, wherein the cap is configured to be opened, allowing the topical formulation to be transferred into the compartment, and wherein the cap is configured to be closed, allowing the topical formulation to be contained therein.

6. The device of claim 1, wherein the compartment is a unitary piece or formed by two or more separate parts.

7. The device of claim 6, wherein the cap is attached to a portion of the side wall of the compartment via a hinge and is able to open and close via the hinge.

8. The device of claim 6, wherein the cap is removable from the rest of the device.

9. The device of claim 8, wherein each of the cap and the side wall comprises mating threads and the cap attaches to the side wall via the mating threads.

10. The device of claim 1, wherein the cap of the compartment comprises an inlet connector configured to mate with the outlet of a container containing the topical formulation, and wherein the inlet connector comprises an inlet opening that is in fluid communication with the inside of the compartment.

11. The device of claim 1, further comprising a protective layer covering the adhesive coating on the back side of the flexible material.

12. A kit comprising the device of claim 1 and a container containing a topical formulation.

13. A method of delivering a topical formulation comprising one or more local anesthetics, to an implanted port site on the skin of a patient using the device of claim 1 comprising:
    placing the device onto the patient's skin such that the opening of the compartment is exposed to the port site;
    applying pressure to the adhesive coating on the back side of the flexible material to adhere the device to the patient's skin.

14. The device of claim 1,
    wherein the flexible material comprises an attachment portion,
    wherein a second adhesive coating is on the attachment portion of the flexible material,
    wherein the attachment portion is on the back side of the flexible material, wherein the second adhesive coating is the same as or different from the adhesive coating, wherein the flange is attached to the attachment portion of the flexible material, and wherein the cap is attached to a portion of the side wall of the compartment via a hinge and is able to open and close via the hinge.

15. The kit of claim 12, comprising a plurality of the device of claim 1.

16. The method of claim 13, further comprising filling the compartment with the topical formulation.

\* \* \* \* \*